(12) United States Patent
Propst et al.

(10) Patent No.: US 11,278,496 B2
(45) Date of Patent: *Mar. 22, 2022

(54) CRYSTALLINE MICROSPHERES AND THE PROCESS OF MANUFACTURING THE SAME

(71) Applicant: SPI Pharma, Inc., Wilmington, DE (US)

(72) Inventors: Cecil W. Propst, Norton Shores, MI (US); Marc W. Meadows, Grand Haven, MI (US); Michael S. Todd, Grand Haven, MI (US)

(73) Assignee: SPI Pharma, Inc., Wilmington, DE (US)

( * ) Notice: Subject to any disclaimer, the term of this patent is extended or adjusted under 35 U.S.C. 154(b) by 12 days.

This patent is subject to a terminal disclaimer.

(21) Appl. No.: 16/371,262

(22) Filed: Apr. 1, 2019

(65) Prior Publication Data

US 2019/0224126 A1  Jul. 25, 2019

Related U.S. Application Data

(63) Continuation of application No. 14/809,362, filed on Jul. 27, 2015, now Pat. No. 10,245,232, which is a continuation of application No. 13/870,556, filed on Apr. 25, 2013, now Pat. No. 9,089,487.

(60) Provisional application No. 61/783,603, filed on Mar. 14, 2013, provisional application No. 61/638,073, filed on Apr. 25, 2012.

(51) Int. Cl.
*A61K 9/16* (2006.01)

(52) U.S. Cl.
CPC .............. *A61K 9/1623* (2013.01); *A61K 9/16* (2013.01); *Y10T 428/2982* (2015.01)

(58) Field of Classification Search
CPC .... A61K 9/1623; A61K 9/16; Y10T 428/2982
See application file for complete search history.

(56) References Cited

U.S. PATENT DOCUMENTS

| | | | |
|---|---|---|---|
| 4,820,627 A | 4/1989 | McGeehan | |
| 5,679,398 A | 10/1997 | Serpelloni et al. | |
| 5,780,055 A | 7/1998 | Habib et al. | |
| 6,235,947 B1 * | 5/2001 | Yoshinari | C07C 29/78 546/342 |
| 6,248,363 B1 | 6/2001 | Patel et al. | |
| 6,264,989 B1 | 7/2001 | Kato et al. | |
| 6,692,768 B1 | 2/2004 | Ishibashi et al. | |
| 6,855,361 B2 | 2/2005 | Rapp et al. | |
| 7,118,765 B2 | 10/2006 | Norman et al. | |
| 7,582,154 B2 | 9/2009 | Propst et al. | |
| 7,625,507 B2 | 12/2009 | Ray et al. | |
| 8,545,889 B2 | 10/2013 | Norman et al. | |
| 8,617,588 B2 | 12/2013 | Tillotson et al. | |
| 9,089,487 B2 | 7/2015 | Propst et al. | |
| 2003/0129250 A1 * | 7/2003 | Batycky | A61K 9/1652 424/490 |
| 2006/0024379 A1 * | 2/2006 | Brown | A61K 9/0019 424/490 |
| 2006/0057213 A1 * | 3/2006 | Larhrib | A61K 9/0075 424/489 |
| 2006/0263423 A1 | 11/2006 | Norman et al. | |
| 2007/0092562 A1 | 4/2007 | Norman et al. | |
| 2008/0107729 A1 | 5/2008 | Amin et al. | |
| 2008/0181932 A1 | 7/2008 | Bortz et al. | |
| 2010/0068276 A1 | 3/2010 | Friesen et al. | |
| 2010/0092568 A1 | 4/2010 | Lerner et al. | |
| 2010/0167052 A1 * | 7/2010 | Satomi | A23L 29/37 428/402 |
| 2010/0247665 A1 | 9/2010 | Takahashi | |
| 2011/0135927 A1 | 6/2011 | Salomi et al. | |
| 2011/0269874 A1 | 11/2011 | Mukai et al. | |
| 2014/0023707 A1 | 1/2014 | Norman et al. | |
| 2014/0044793 A1 | 2/2014 | Goll et al. | |
| 2014/0093574 A1 | 4/2014 | Tillotson et al. | |
| 2014/0099372 A1 | 4/2014 | Propst et al. | |
| 2015/0140097 A1 | 5/2015 | Propst et al. | |

FOREIGN PATENT DOCUMENTS

| | | |
|---|---|---|
| EP | 0913148 | 5/1999 |
| EP | 0812187 | 5/2003 |
| JP | H1-092403 | 4/1999 |

(Continued)

OTHER PUBLICATIONS

P. Kippax, "Particle size analysis," PharmTech.com Advancing Development and Manufacturing, Pharmaceutical Technology Europe PTE, vol. 21, Issue 4, <http://www.pharmtech.com/particle-size-analysis?id=&sk=&date=&&pageID=1>, Apr. 1, 2009, p. 1-4.*

Z. Sun et al., "Particle Size Specifications for Solid Oral Dosage Forms: A Regulatory Perspective," American Pharmaceutical Review, May 1, 2010, <http://www.americanpharmaceuticalreview.com/Featured-Articles/36779-Particle-Size-Specifications-for-Solid-Oral-Dosage-Forms-A-Regulatory-Perspective/>, p. 1-10.*

S. Adi et al., "Agglomerate strength and dispersion of pharmaceutical powders," Journal of Aerosol Science 42 (2011) pp. 285-294.*

Notification of Reasons for Rejection, dated Dec. 1, 2017, for Japanese Patent Application No. 2015-509147, with English translation.

Clinic All-Round, 1999, vol. 48, No. 6, pp. 1577-1578.

(Continued)

*Primary Examiner* — Monica A Shin
(74) *Attorney, Agent, or Firm* — Morgan, Lewis & Bockius LLP

(57) ABSTRACT

Microspheres comprising a core material, wherein the microspheres have a circularity greater than 0.95 and an aspect ratio greater than 0.95, and methods of manufacturing the same. The microspheres may be useful in the manufacture of sustained and modified release active pharmaceutical ingredient (API) microspheres, as a free flowing excipient for mini-tablets and in the manufacture of API dispersions.

20 Claims, 22 Drawing Sheets

(16 of 22 Drawing Sheet(s) Filed in Color)

(56) References Cited

FOREIGN PATENT DOCUMENTS

| | | |
|---|---|---|
| JP | 2007-508240 | 4/2007 |
| JP | 2007-217651 | 8/2007 |
| JP | 2009-544812 | 12/2009 |
| JP | 2011-157348 | 8/2011 |
| WO | 02/035991 A2 | 5/2002 |
| WO | 2005/009375 | 2/2005 |
| WO | 2008/016684 A1 | 2/2008 |
| WO | 2008/146590 | 12/2008 |
| WO | 2010/128300 A1 | 11/2010 |
| WO | 2010/021300 A1 | 1/2012 |
| WO | 2012/036953 | 3/2012 |

OTHER PUBLICATIONS

J. Pharmacol. Exp. Ther., 1977, vol. 201, No. 3, pp. 762-768.
Examination Report, dated Dec. 19, 2017, for Indian Patent Application No. 9416/DELNP/2014.
Translation of Official Action for Mexican Patent Application No. MX/a/2014/012805.
Office Action, dated May 31, 2017, for co-pending U.S. Appl. No. 14/397,011.
Notification of Reasons for Rejection, dated Jan. 11, 2017, for Japanese Patent Application No. 2015-509147, with English translation.
Examination Report, dated Dec. 11, 2015, for Canadian Patent Application No. 2,871,429.
Non-Final Office Action, dated Aug. 18, 2016, for co-pending U.S. Appl. No. 14/397,011.
Non-Final Office Action, dated May 6, 2014, for parent U.S. Appl. No. 13/870,556.
Final Office Action, dated Sep. 16, 2014, for parent U.S. Appl. No. 13/870,556.
Examination Report, dated Jun. 22, 2016, for Canadian Patent Application No. 2,871,429.
Non-Final Office Action, dated Nov. 18, 2015, for co-pending U.S. Appl. No. 14/397,011.
Extended European Search Report for European Patent Application No. 13781897.7, dated Aug. 18, 2015.
Chambi et al., "Solid lipid microparticles containing water-soluble compounds of different molecular mass: Production, characterisation and release profiles." Food Research International 41 (2008) 229-236.
Luciani et al., "Solvent and melting induced microspheres sintering techniques: a comparative study of morphology and mechanical properties." J Mater Sci: Mater Med (2011) 22:2019-2028.
International Search Report and Written Opinion dated Sep. 13, 2013 for International Application No. PCT/US2013/038257.
Hideki Takahashi, "Properties of spherical mannitol on pharmaceutical preparation." Pharm Tech Japan, vol. 27, No. 12 (2011), 15(2361)-17(2363).
S. Adi et al., "Agglomerate strength and dispersion of pharmaceutical powders," Journal of Aerosol Science 42 (2011) 285-294.
P. Kippax, "Particle size analysis," PharmTech.com Advancing Development and Manufacturing, Pharmaceutical Technology Europe PTE, vol. 21, Issue 4, <http://www.pharmtech.com/particle-size-analysis?d=&sk=&date=&&page1D=1 >, Apr. 1, 2009, p. 1-4.
Technical Report for Brazilian Patent Application No. BR112014026351-5, dated Jul. 26, 2019 (with translation).
Decision of Refusal for Japanese Patent Application No. 2015-509147, dated Nov. 9, 2018 (with translation).
Search Report and Opinion for European Patent Application No. 19163519.2, dated Nov. 27, 2019.

* cited by examiner

Circularity

Periphery of a circle of similar area/ real periphery
(Total # of pixels as area in equation/ actual count of pixels on periphery)

Area
14*3=42
13*7=91
8
5  or total of 144 pixels $$Sphericity = \frac{2\sqrt{\pi * Pixel\_Area}}{P_{real}} = \frac{42.5}{48} = .886$$

Periphery
8+2+1+9+1+8+4+2+3+4+3+1+2=48

Aspect Ratio

Shortest Feret diameter/longest Feret diameter

12/14 = 0.857

Aspect Ratio = L / T

CRYSTALLINE MICROSPHERES AND THE PROCESS OF MANUFACTURING THE SAME

CROSS-REFERENCE TO RELATED APPLICATIONS

This application is a continuation of U.S. patent application Ser. No. 14/809,362 filed on Jul. 27, 2015, which is a continuation of U.S. patent application Ser. No. 13/870,556 filed on. Apr. 25, 2013, which claims priority to U.S. Provisional Application No. 61/638,073 filed Apr. 25, 2012 and U.S. Provisional Application No. 61/783,603 filed Mar. 14, 2013, all of which are hereby incorporated by reference in their entireties.

FIELD OF THE INVENTION

The present invention relates to microspheres comprising a core material, wherein the microsphere is perfectly spherical, and the method of manufacturing the same. The present invention is useful in the manufacture of sustained and modified release active pharmaceutical ingredient (API) microspheres, as a free flowing excipient for mini-tablets and in the manufacture of API carrier dispersions.

BACKGROUND OF THE INVENTION

Many commercial pharmaceutical beads are either reactive or insoluble. Reactive beads such as sucrose/starch beads can cause incompatibility with active substances and loss of active substance due to the presence of reducing sugars. Reaction of moisture in beads made with microcrystalline cellulose, sucrose, starch or cellulose derivatives containing beads can cause incompatibility with active substances and loss of active substance due to the presence of moisture. Loss of API in insoluble beads such as those made with microcrystalline cellulose, starch or cellulose derivatives can result in lack of release of active substance or lower extraction yields from the insoluble materials due to the of insoluble matrixes. Beads made with soluble components such as polyols can be made with very low moisture content (anhydrous) and can be made completely soluble.

Current polyol beads are granulated, thus undissolved polyol particles, primary particles, are "glued" together with a binder solution to make a secondary granular structure. This process makes a surface that is only as smooth and durable as the starting particle size and as the shape will allow. The starting material is not completely liquefied as some remain solid in the granulation route approach and thus transitions are present. Also for very small spheres the contour of the starting particle contributes to a lack of having a smooth crevice-free and bump-free surface, thus lacking perfectly shaped solid spheres. Because the binder contains a solvent, the wet beads must be dried. Bead drying can create internal porosity as well as transition layers of insoluble materials between the undissolved bodies we are calling primary particles. Formation of a wet mass is often done using a granulator, followed by an extruder to form a dense packed pellet and then spinning the pellet on a friction plate into a sphere. Formation can also be done by a powder layering process on a core particle or bead that needs to be large enough to maintain separation in the coating process. This required core and the need to maintain separation restricts the size of the bead that can be made. The layering process starts with seed core upon which insoluble primary particles are deposited and bonded using the binder solution. For effective layering the primary particles must be small enough (<10 μm for 150 μm sphere) to be formed into a reasonably smooth surfaced sphere (<30 μm for 300 μm sphere). The primary layering particles and the layer application amount must be small enough to prevent porosity and/or moisture from being trapped deep in the sphere. Drying during layering process is critical to balance enough wetness for growth, bead strength and dryness for reduced interior moisture and prevent vacuoles/residual porosity. A water insoluble wicking agent such as MCC aides in the removal of moisture but is insoluble. Final bead size is limited to spheres larger than 100 μm mean size (10 μm primary layering particle size) to allow granular shaping and maintain bead separation (preventing twins) during the layering process.

Commercially available beads used as cores as API delivery beads in applications that can survive the temperature/tumbling conditions of the API coating and layering process are larger than 100 μm (mean particle diameter). Tablets containing API delivery beads incorporated and compressed into tablets require smaller size beads if bead crushing/rupturing of the functional coating on coated bead during tablet compression is to be avoided. Tablets containing beads are made typically into swallow tablets to avoid chewing, thus tablet thickness needs to be small to allow ease of swallowing. Beads need to be cushioned during tablet compression to prevent them from being crushed with larger bead requiring more cushioning materials. Larger beads place limitations on the tableting process (slower press speed) and formulation (requires more crushing agents) to create an environment that prevents bead fracturing of larger beads. Smaller beads thus allow for smaller tablets, less cushioning ingredients to be required in tablet formulation as well as in the coating layers and higher dose loading of API.

Excipients for very small mini-tablets (<3 mm in tablet diameter), require very small excipient particles for fill/tablet weight control. A 1/50 of the diameter of the tablet standard for particle size would require a particle size mean of 60 μm. Current<90 μm particles of microcrystalline cellulose (MCC) (and milled MCC<90 μm) are used. These materials are not spherical and thus prone to flow issues causing weight uniformity issues, especially at faster tablet press speeds.

SUMMARY OF THE INVENTION

In some embodiments, the present invention provides for improved microspheres that can be 100% soluble, perfectly spherical, have a uniform surface with limited<2 micron peak to valley roughness, be as small as 10 μm, be comprised in some embodiments of a single crystal structure with limited or no internal voids, have low hygroscopicity, and low moisture content of less than 1%.

In some embodiments, the present invention relates to improved microspheres comprising a core material, wherein the microsphere is perfectly spherical, and the method of manufacturing the same. In some embodiments, the present invention relates to improved microspheres comprising a core material, wherein the microsphere is perfectly spherical and has a moisture content less than 1%. In some embodiments, the present invention relates to improved pharmaceutical microspheres comprising a core material, wherein the microsphere is perfectly spherical, has a smooth surface and has a moisture content less than 1%.

In some embodiments, the present invention relates to improved microspheres comprising a core material, wherein the microsphere is perfectly spherical, has low hygroscopicity, and has a moisture content less than 1%.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing summary, as well as the following detailed description of the invention, will be better understood when read in conjunction with the appended drawings. For the purpose of illustration the invention, there are shown in the drawings embodiments which are presently preferred. It should be understood, however, that the invention can be embodied in different forms and thus should not be construed as being limited to the embodiments set forth herein.

DETAILED DESCRIPTION OF INVENTION

Figure 1:
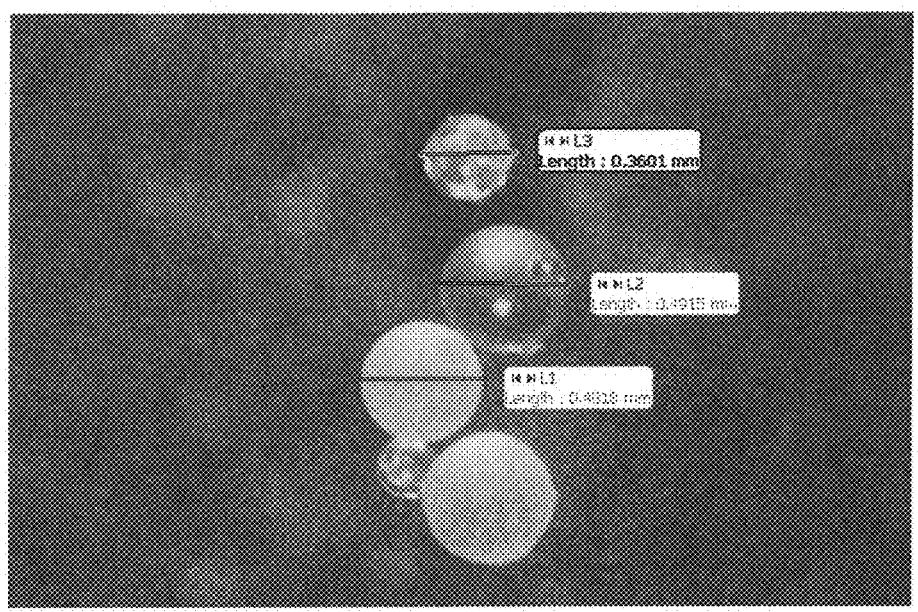
FIG. 1 is a photomicrograph of exemplary mannitol microspheres of the present invention.

The following detailed description is exemplary and explanatory and is intended to provide further explanation of the invention described herein. Other advantages, and novel features will be readily apparent to those skilled in the art from the following detailed description of the invention.

The present invention is described herein using several definitions, as set forth below and throughout the application.

Definitions

The term "about" will be understood by persons of ordinary skill in the art and will vary to some extent on the context in which it is used. If there are uses of the term which are not clear to persons of ordinary skill in the art given the context in which it is used, "about" shall mean up to plus or minus 10% of the particular value.

The terms "solid dosage form," "tablet," and "solid preparation" are used synonymously within the context of the present invention. These terms should be construed to include a compacted or compressed powder composition obtained by compressing or otherwise forming the composition to form a solid having a defined shape.

The aim of the present invention was to overcome the drawbacks of existing commercial beads.

In one embodiment, the present invention relates to a microsphere comprising a core material, wherein the microsphere has perfect sphericity. "Perfect sphericity" or "perfectly spherical" means a circularity as measured by imaging microscopy of greater than 0.90, and an aspect ratio of less than 1.0. In some embodiments, the microspheres have a circularity greater than 0.91. In some embodiments, the microspheres have a circularity greater than 0.92. In some embodiments, the microspheres have a circularity greater than 0.93. In some embodiments, the microspheres have a circularity greater than 0.94. In some embodiments, the microspheres have a circularity greater than 0.95. In some embodiments, the microspheres have a circularity greater than 0.96. In some embodiments, the microspheres have a circularity greater than 0.97. In some embodiments, the microspheres have a circularity greater than 0.98. Circularity is calculated in accordance with International Organization for Standardization (ISO) 9276-6.

In some embodiments, the microspheres have an aspect ratio of 0.90. In some embodiments, the microspheres have an aspect ratio of 0.91. In some embodiments, the microspheres have an aspect ratio of 0.92. In some embodiments, the microspheres have an aspect ratio of 0.93. In some embodiments, the microspheres have an aspect ratio of 0.94. In some embodiments, the microspheres have an aspect ratio of 0.95. In some embodiments, the microspheres have an aspect ratio of 0.96. In some embodiments, the microspheres have an aspect ratio of 0.97. In some embodiments, the microspheres have an aspect ratio of 0.98. In some embodiments, the microspheres have an aspect ratio of 0.99. In some embodiments, the microspheres have an aspect ratio of 1.0. In some embodiments, the microspheres have an aspect ratio of 0.90 or greater. In some embodiments, the microspheres have an aspect ratio of 0.91 or greater. In some embodiments, the microspheres have an aspect ratio of 0.92 or greater. In some embodiments, the microspheres have an aspect ratio of 0.93 or greater. In some embodiments, the microspheres have an aspect ratio of 0.94 or greater. In some embodiments, the microspheres have an aspect ratio of 0.95 or greater. In some embodiments, the microspheres have an aspect ratio of 0.96 or greater. In some embodiments, the microspheres have an aspect ratio of 0.97 or greater. In some embodiments, the microspheres have an aspect ratio of 0.98 or greater. In some embodiments, the microspheres have an aspect ratio of 0.99 or greater. Aspect Ratio is calculated in accordance with International Organization for Standardization (ISO) 9276-6 (2008).

In some embodiments of the present invention, microspheres have a convexity ratio of 0.99. In some embodiments, 30% of microspheres have a convexity ratio of 0.99. In some embodiments, 40% of microspheres have a convexity ratio of 0.99. In some embodiments, 50% of microspheres have a convexity ratio of 0.99. In some embodiments, 60% of microspheres have a convexity ratio of 0.99. In some embodiments, 70% of microspheres have a convexity ratio of 0.99. In some embodiments, 80% of microspheres have a convexity ratio of 0.99. In some embodiments, 30% or more of microspheres have a convexity ratio of 0.99. In some embodiments, 40% or more of microspheres have a convexity ratio of 0.99. In some embodiments, 50% or more of microspheres have a convexity ratio of 0.99. In some embodiments, 60% or more of microspheres have a convexity ratio of 0.99. In some embodiments, 70% or more of microspheres have a convexity ratio of 0.99. In some embodiments, 80% or more of microspheres have a convexity ratio of 0.99. Convexity Ratio is calculated in accordance with International Organization for Standardization (ISO) 9276-6 (2008).

In some embodiments of the present invention, microspheres have a solidity ratio of 0.99. In some embodiments, 30% of microspheres have a solidity ratio of 0.99. In some embodiments, 40% of microspheres have a solidity ratio of 0.99. In some embodiments, 50% of microspheres have a solidity ratio of 0.99. In some embodiments, 60% of microspheres have a solidity ratio of 0.99. In some embodiments, 70% of microspheres have a solidity ratio of 0.99. In some embodiments, 80% of microspheres have a solidity ratio of 0.99. In some embodiments, 90% of microspheres have a solidity ratio of 0.99. In some embodiments, 30% or more of microspheres have a solidity ratio of 0.99. In some embodiments, 40% or more of microspheres have a solidity ratio of 0.99. In some embodiments, 50% or more of microspheres have a solidity ratio of 0.99. In some embodiments, 60% or more of microspheres have a solidity ratio of 0.99. In some embodiments, 70% or more of microspheres have a solidity ratio of 0.99. In some embodiments, 80% or more of microspheres have a solidity ratio of 0.99. In some embodiments, 90% or more of microspheres have a solidity ratio of 0.99. Solidity Ratio is calculated in accordance with International Organization for Standardization (ISO) 9276-6 (2008).

In some embodiments of the present invention, a microsphere has a mean particle size from about 2 µm to about 1500 µm. In some embodiments of the present invention, a microsphere has a mean particle size from about 2 µm to about 10 µm. In some embodiments of the present invention, a microsphere has a mean particle size from about 10 µm to about 20 µm. In some embodiments of the present invention, a microsphere has a mean particle size from about 10 µm to about 500 µm. This mean particle size d(0.5) can be anywhere within this range based on process flow conditions chosen. In one embodiment of the present invention, a microsphere has a particle size distribution (d(0.9)/d(0.1)) of 2.8 or less. In another embodiment of the present invention, a microsphere has a particle size distribution of 2.7 or less. In another embodiment of the present invention, a microsphere has a particle size distribution of 2.4 or less. In another embodiment of the present invention, a microsphere has a particle size distribution of 2.3 or less. In another embodiment of the present invention, a microsphere has a particle size distribution of 2.2 or less. In another embodiment of the present invention, a microsphere has a particle size distribution of 2.1 or less. In another embodiment of the present invention, a microsphere has a mean particle size distribution of 2.0 or less. In another embodiment of the present invention, a microsphere has a particle size distribution of 1.9 or less. In another embodiment of the present invention, a microsphere has a particle size distribution of 1.8 or less.

In some embodiments, the perfect sphericity, perfect solidity, narrow particle density and lack of pores of the microspheres of the present invention create the ability to use size selection to narrowly control the effective surface area (ESA) for coating the microspheres per mass. The effective surface area is the surface at the base of the functional film or coating whose thickness for performance is fixed at a minimum and a maximum. Normal for functional films or coating, the thickness required is a film or coating of 10 µm or more. If substantially all of the surface of the microsphere is part of the start of the functional thickness layering it is as if the coating or film is being applied to a flat surface. Thus the build of thickness is uniform and reproducible. Coating lost into pores or needed over risers is not lost if the microsphere has both a high solidity and a high convexity value. The surface area for the weight of beads used in the coating batch can thus be related directly to bead size and bead size frequency even down to 10 µm beads. Factors of shape, bead density, and effective surface lost into crevices and pores and surface distortions from risers are no longer factors that affect the relationship of size selection to the effective surface per batch to be coated. Also particle flow of a circular microsphere at 10 µm is maintained as particles are spherical and particle to particle contact is at points of contact and thus minimal surface area involved. In some embodiments, minimal moisture<0.2% generates a very small surface free energy at contact points. In some embodiments, microspheres of the present invention also can be made static free as the process is a crystallization process, even at the 10 µm level. Maintaining separation is extremely important to prevent agglomeration during coating and use. Aerodynamics is also uniform based on the microspheres having uniform shape and density. In some embodiments, submicron crystal ridges exist even on the 10 µm microsphere thus even though the microsphere appears smooth the surface can be attached to with coating materials.

In some embodiments, the present invention provides for the manufacture of microspheres that have a standardizable surface area, due to their perfectly spherical shape and their lack of internal porosity. In some embodiments of the present invention, the microsphere lacks internal porosity. In some embodiments, the microsphere lacks internal voids. A void is defined as an area in the bead that is not open to the surface and thus not a pore. This open area normally filled with air causes the density of the particle to be lowered when present. If present, these pores create particle density variability as their presence is usually not uniform. Thus in process using sonic nozzles or using a size selection process a specific narrow range of surface area/process weight used will allow coating a much more exact surface area and the variability of film thickness controlled. Current commercial beads are made and available in size ranges. In some embodiments, the present invention provides for the manufacture and/or sorting of microspheres to provide microspheres of a standard surface and much more narrowed surface area range per weight of beads used per batch for coating process. This provides for a uniformly coated microsphere and narrows the distribution of coating film thicknesses from batch to batch.

In some embodiments of the present invention, a microsphere has a smooth surface. A smooth surface with lack of bumps is essential for uniformity in the coating thickness of an API and decreasing the risk of pin hole formations in the coating film. However small ridges in the microsphere surface aide in the adherence of binder or coating solution to the surface of the microsphere. In one embodiment, a microsphere has a surface with ridges of 10 µm or less in size. In one embodiment, a microsphere has a surface with ridges of 9 µm or less in size. In one embodiment, a microsphere has a surface with ridges of 8 µm or less in size. In one embodiment, a microsphere has a surface with ridges of 7 µm or less in size. In one embodiment, a microsphere has a surface with ridges of 6 µm or less in size. In one embodiment, a microsphere has a surface with ridges of 5 µm or less in size. In one embodiment, a microsphere has a surface with ridges of 4 µm or less in size. In one embodiment, a microsphere has a surface with ridges of 3 µm or less in size. In one embodiment, a microsphere has a surface with ridges of 2 µm or less in size. In one embodiment, a microsphere has a surface with ridges of 1 µm or less in size. In one embodiment, a microsphere has a surface with ridges of <10 µm in size. In one embodiment, a microsphere has a surface with ridges of <9 µm in size. In one embodiment, a microsphere has a surface with ridges of <8 µm in size. In one embodiment, a microsphere has a surface with ridges of <7 µm in size. In one embodiment, a microsphere has a surface with ridges of <6 µm in size. In one embodiment, a microsphere has a surface with ridges of <5 µm in size. In one embodiment, a microsphere has a surface with ridges of <4 µm in size. In one embodiment, a microsphere has a surface with ridges of <3 µm in size. In one embodiment, a microsphere has a surface with ridges of <2 µm in size. In one embodiment, a microsphere has a surface with ridges of <1 µm in size.

In some embodiments of the present invention, a microsphere has a skeletal density of about 1.4595 to about 1.4651 gm/cc by helium pynometry. This is compared to the true density by x-ray diffraction of a polyol alpha mannitol crystal form found of 1.468 gm/ml. This develops a bead porosity of (1.468-1.4595)/1.468 of 0%. This crystal lattice density matches the DSC scan for beads showing a match of crystal energy of alpha mannitol and the melting point match to alpha mannitol identifies these beads a solid crystal alpha mannitol forms.

In some embodiments of the present invention, a microsphere has low hygroscopicity. In one embodiment, a microsphere has moisture gain of 0.18% at 90% relative humidity. In one embodiment, a microsphere has moisture gain of <2.0% at 90% relative humidity. In one embodiment, a microsphere has moisture gain of <1.9% at 90% relative humidity. In one embodiment, a microsphere has moisture gain of <1.8% at 90% relative humidity. In one embodiment, a microsphere has moisture gain of <1.7% at 90% relative humidity. In one embodiment, a microsphere has moisture gain of <1.6% at 90% relative humidity. In one embodiment, a microsphere has moisture gain of <1.5% at 90% relative humidity. In one embodiment, a microsphere has moisture gain of <1.4% at 90% relative humidity. In one embodiment, a microsphere has moisture gain of <1.3% at 90% relative humidity. In one embodiment, a microsphere has moisture gain of <1.2% at 90% relative humidity. In one embodiment, a microsphere has moisture gain of <1.1% at 90% relative humidity. In one embodiment, a microsphere has moisture gain of <1.0% at 90% relative humidity. In one embodiment, a microsphere has moisture gain of <0.9% at 90% relative humidity. In one embodiment, a microsphere has moisture gain of <0.8% at 90% relative humidity. In one embodiment, a microsphere has moisture gain of <0.7% at 90% relative humidity. In one embodiment, a microsphere has moisture gain of <0.6% at 90% relative humidity. In one embodiment, a microsphere has moisture gain of <0.5% at 90% relative humidity. In one embodiment, a microsphere has moisture gain of <0.4% at 90% relative humidity. In one embodiment, a microsphere has moisture gain of <0.3% at 90% relative humidity. In one embodiment, a microsphere has moisture gain of <0.2% at 90% relative humidity. In one embodiment, a microsphere has moisture gain of <0.1% at 90% relative humidity. In one embodiment, a microsphere has moisture gain of <0.05% at 90% relative humidity. In one embodiment, a microsphere has moisture gain of 0% at 90% relative humidity.

In another embodiment, a microsphere has a moisture gain of <1.00% at 60% relative humidity. In another embodiment, a microsphere has a moisture gain of <0.90% at 60% relative humidity. In another embodiment, a microsphere has a moisture gain of <0.80% at 60% relative humidity. In another embodiment, a microsphere has a moisture gain of <0.70% at 60% relative humidity. In another embodiment, a microsphere has a moisture gain of <0.60% at 60% relative humidity. In another embodiment, a microsphere has a moisture gain of <0.50% at 60% relative humidity. In another embodiment, a microsphere has a moisture gain of <0.40% at 60% relative humidity. In another embodiment, a microsphere has a moisture gain of <0.30% at 60% relative humidity. In another embodiment, a microsphere has a moisture gain of <0.20% at 60% relative humidity. In another embodiment, a microsphere has a moisture gain of <0.10% at 60% relative humidity. In another embodiment, a microsphere has a moisture gain of <0.09% at 60% relative humidity. In another embodiment, a microsphere has a moisture gain of <0.08% at 60% relative humidity. In another embodiment, a microsphere has a moisture gain of <0.07% at 60% relative humidity. In another embodiment, a microsphere has a moisture gain of <0.06% at 60% relative humidity. In another embodiment, a microsphere has a moisture gain of <0.05% at 60% relative humidity. In another embodiment, a microsphere has a moisture gain of <0.04% at 60% relative humidity. In another embodiment, a microsphere has a moisture gain of <0.03% at 60% relative humidity. In another embodiment, a microsphere has a moisture gain of <0.02% at 60% relative humidity. In another embodiment, a microsphere has a moisture gain of <0.01% at 60% relative humidity. In another embodiment, a microsphere has a moisture gain of 0% at 60% relative humidity. Hygroscopicity is measured by Dynamic Vapor Sorption (DVS).

In some embodiments of the present invention, a microsphere has a moisture content of 2.0% or less. In one embodiment, a microsphere has a moisture content of 1.9% or less. In one embodiment, a microsphere has a moisture content of 1.8% or less. In one embodiment, a microsphere has a moisture content of 1.7% or less. In one embodiment, a microsphere has a moisture content of 1.6% or less. In one embodiment, a microsphere has a moisture content of 1.5% or less. In one embodiment, a microsphere has a moisture content of 1.4% or less. In one embodiment, a microsphere has a moisture content of 1.3% or less. In one embodiment, a microsphere has a moisture content of 1.2% or less. In one embodiment, a microsphere has a moisture content of 1.1% or less. In one embodiment, a microsphere has a moisture content of 1.0% or less. In one embodiment, a microsphere has a moisture content of 0.9% or less. In one embodiment, a microsphere has a moisture content of 0.8% or less. In one embodiment, a microsphere has a moisture content of 0.7% or less. In one embodiment, a microsphere has a moisture content of 0.6% or less. In one embodiment, a microsphere has a moisture content of 0.5% or less. In one embodiment, a microsphere has a moisture content of 0.4% or less. In one embodiment, a microsphere has a moisture content of 0.3% or less. In one embodiment, a microsphere has a moisture content of 0.2% or less. In one embodiment, a microsphere has a moisture content of 0.1% or less. In one embodiment, a microsphere has a moisture content of 0.09% or less. In one embodiment, a microsphere has a moisture content of 0.08% or less. In one embodiment, a microsphere has a moisture content of 0.07% or less. In one embodiment, a microsphere has a moisture content of 0.06% or less. In one embodiment, a microsphere has a moisture content of 0.05% or less. In one embodiment, a microsphere has a moisture content of 0.04% or less. In one embodiment, a microsphere has a moisture content of 0.03% or less. In one embodiment, a microsphere has a moisture content of 0.02% or less. Moisture content is measured by loss on drying using Karl Fisher method. Hygroscopicity and moisture content are important characteristics of microspheres or beads as they may affect changes in active pharmaceutical ingredients (APIs), such as amorphous APIs, APIs sensitive to hydration, micronized and freeze-dried APIs that are sensitive to moisture.

In some embodiments of the present invention, a microsphere is water soluble. Insoluble materials can interfere with the full delivery of an API. Insoluble materials can also become an issue in the formation of complete solutions, plugging needles and filters.

In some embodiments of the present invention, a microsphere comprises a single core material. In another embodiment, a microsphere comprises a core material, wherein the core material is a polyol. In another embodiment, a microsphere comprises a core material, wherein the core material is mannitol. In another embodiment, a microsphere comprises a core material, wherein the core material is 100% mannitol. In another embodiment, a microsphere comprises a core material, wherein the core material is sorbitol. In another embodiment, a microsphere comprises a core material, wherein the core material is maltitol. In another embodiment, a microsphere comprises a core material, wherein the core material is erythritol. In another embodiment, a microsphere comprises a core material, wherein the core material is xylitol. In another embodiment, a microsphere comprises one or more core materials. In some embodiments of the present invention, a microsphere has a crystalline structure.

Core Material

In some embodiments, microspheres of the present invention can be comprised of many different core materials including, but not limited to, carbohydrates, polyols, sugars, starches, waxes, polyethylene glycol, cetyl alcohol, stearic acid, fatty acids, fatty acid esters, polyethylene glycol derivatives, materials miscible with these materials, or combinations thereof. In some embodiments, microspheres of the present invention can be comprised of one or more materials that melt. In some embodiments, microspheres of the present invention can be comprised of a material that is solid at room temperature. In some embodiments, microspheres of the present invention can be comprised of one or materials that are crystalline solid at room temperature and amorphous materials such as melts.

In some embodiments, microspheres of the present invention can also contain additives including, but not limited to, maltodextrins, microcrystalline cellulose, hydroxypropyl methyl cellulose, methyl cellulose, polyvinyl alcohol, sodium CMC, povidone and other vinyl derivatives, calcium carbonate, tartaric acid, alginic acid, talc, titanium oxide, color, flavor, sodium lauryl sulfate, ph adjusters, surface active agents or combinations thereof.

Method of Manufacture

Microspheres of the present invention can be manufactured by various methods. In one embodiment, microspheres can be produced by prilling (spray chilling) of a melt of core material in a stainless steel 2 quart sauce pan. A melted core material is poured into the heated pressure vessel that was heated by electrical heat bands. The heated pressure vessel is pressurized to 50 psig and the plug valve at the bottom of the vessel is opened to send the core material thru the spray line to the nozzle. The spray line is heated by electrical heat tape. The nozzle is heated with a propane torch prior to opening the valve. The prills from the nozzle (Spraying Systems 6501) are collected on plastic and bagged for evaluation.

In another embodiment, microspheres of the present invention can be made by melting a core material and dropping the melt onto a spinning spin disc for formation of microspheres. The core material is melted in a pan or oven at 1° C. to 10° C. or more above its melting point. The core material can also be melted via use of a powder extruder to melt system, such as is available from Randcastle extruders (RCP-1000) to decrease time of core material at melt.

To provide a continuous melt for feeding the spin disc a 5 horsepower horizontal Randcastle RCP-1000 (Cedar Grove, N.J.) melting unit is used. This 36 inch long to 1 inch diameter unit uses a 3:1 ratio compression (0.180" to 0.060" flight depth) single screw microextruder to melt mannitol. Each of the six zones is setup to heat to 340° F. or more in temperature with first three zones at 360° F. Powder is fed with a vibrating feeder tray. Maximum rate of 3.7 kilos per hour is obtained at 178 RPM. Residence time of melt is <2 minutes in unit and flow rate is consistent. Based on this trial a projected 2.5" diameter unit could handle 100 kilos/hour of melt delivery and a 4.5" diameter unit 600 kilos/hour.

In some embodiments, another alternative is to melt core material as a powder in the spin disk head assembly (See Gold Metal Cincinnati Ohio Tornado unit). Once melted, the liquid core material is spun into a stream which, by centrifugal force, is spread into a thin film and exits the disk as a ligament that breaks into droplets or exits as droplets. Surface spinner style disk is preferred with a diameter of 4 inches or more and speed capabilities of from 500 RPM to 11,000 RPM. Wheel RPM controls film thickness and thus droplet/bead/microsphere size. In some embodiments, microspheres are allowed to fall at least 8 feet in room temperature or chilled air to congeal. Once congealed a coarse screen can be used to complete cooling and maintain separation. Any twinning or chill damaged beads are removed with a bead shape shorter.

In another embodiment, microspheres of the present invention can be made by using a sonic nozzle system supplied by Brace (Alzenan, Germany) called the Brace Spherisator M. The unit consists of an oven in which one or two liquid vessels are stored. The oven can be heated to 200° C. Thus isothermal conditions can be maintained on the liquid to 200° C. The bottle(s) containing the liquid(s) can be pressurized. If the head space is pressurized, the liquid will flow to a nozzle which is mounted in a vertical sonicator. Both the amplitude and frequency of the sonic energy can be controlled. The up and down motion as the liquid exits the nozzle causes the liquid stream to separate and form drops. A strobe can be used to see the droplets form. Based on amplitude as a gross adjustment and frequency as the finer adjustment, the droplets release as individuals approximately the size the droplet would be as a cylinder and surface tension then coverts it to a sphere.

In some embodiments, mannitol alone in a single nozzle or an API dissolved in or dispersed in the mannitol melt made into microspheres using this approach produce microspheres either as a pure mannitol microsphere or as a mannitol and API dispersion. Phenytoin, carbamazepine and folic acid are examples of APIs that can be dissolved/dispersed in the melt of mannitol at 180° C. The liquid is delivered from a single sonic nozzle. The nozzle vibrates in an up and down amplitude at a frequency to produce an individual droplet at the tip. The droplet is allowed to cool as it freely falls to form a solidified microsphere. Cooling can occur at room temperature or in a chilled environment. As a signal nozzle setup using a 200 µm nozzle at a flow rate of 35 g/min with the amplitude and frequency set based on a strobe light to maintain droplet formation separation. Pressure on the vessel is maintained to maintain flow rate.

In some embodiments, a core liquid can also be injected in a center nozzle of a two concentric nozzle setup. An example is the 100 µm outer and the 100 µm inner nozzle in the Spherisator M. In some embodiments, the core can be a melted API or a non-volatile liquid containing dissolved API or a nanosized API suspension or mannitol melt or mannitol melt API solution or dispersion. In some embodiments, the core is delivered under pressure from a vessel in an oven to maintain its temperature needed to maintain the melt. In some embodiments, a coating of a melt mannitol alone or coating of an API dissolved or dispersed in the mannitol melt can form the outer shell.

Applications

The microspheres of the present invention are useful in various applications. In one embodiment, the microspheres of the present invention are useful in the manufacture of sustained and modified release beads for dosing active pharmaceutical ingredients (APIs) as multi-particulate systems. In another embodiment, the microspheres of the present invention are useful are carriers for APIs for subsequent manufacture into tablets. In another embodiment, the microspheres of the present invention are useful as a free flowing excipient in the manufacture of mini-tablets. In another embodiment, the microspheres of the present invention are useful in the manufacture of API dispersions.

In some embodiments, microspheres of the present invention are useful as core beads onto which an API is layered either in a suspension or a solution or dry powder alternated with a solution to create a tacky surface and if needed a functional coating also applied. In some embodiments, microspheres of the present invention are useful as core beads for immediate, modified and/or sustain release active and coated beads for inclusion into sachets, capsules and tablet formulations. In some embodiments, microspheres of the present invention are useful as placebo beads. In some embodiments, microspheres of the present invention are useful as cores for plating of APIs onto by lyophilization process.

In some embodiments of the present invention, microspheres can have a small particle size. In some embodiments, such microspheres of the present invention are useful for sachets and chewable tablets to reduce damage [to the API] during chewing, and to improve the mouthfeel of the tablet. In some embodiments, such microspheres are useful in all dosage forms to reduce final bead size yet allow for high API dose loading. In some embodiments, such microspheres are useful as they may allow for a greater thickness of API coating and thus a wider range of release rate options for use of thicker coatings giving a slower release. In some embodiments, such small microspheres are useful as they may reduce localized concentration of irritative drug by providing greater surface area. In some embodiments, small microspheres are useful as they may reduce variation in gastric emptying rate and transit time. In some embodiments, small microspheres are useful as they are less susceptible to dose dumping. In some embodiments, small microspheres are useful as they disperse more freely in gastrointestinal tract and invariably maximize API absorption and also reduce peak plasma fluctuation. In some embodiments, small microspheres are useful as they can be used as a free flowing excipient in mini-tablets.

Compositions

In some embodiments of the present invention, compositions comprise a microsphere of the present invention and an active pharmaceutical ingredient (API). APIs useful in the present invention may include but are not limited to those described in the *Physician's Desk Reference,* 61st ed. Montvale, N.J.: Thomson PDR; 2007, which is incorporated by reference herein in its entirety. In some embodiments, the API may be present inside the microsphere. In another embodiment, the API may be present on the outside of the microsphere. The microspheres of the present invention are useful in combination with standard methods of API incorporation into or onto beads or microspheres.

In some embodiments of the present invention, a blend of powder of a core material and an API can be added to a melt extruder and once melted would disperse in melt and discharge as a melt stream either to be pressure atomized to or a spin disc for creation of microspheres. In another embodiment, an API can be dissolved in a melted core material. In another embodiment, a second feeder position can be added to a two-stage melt extruder wherein the melt flowing at a controlled rate based on RPM of the melt extruder push melt past a powder entry point where a mixture of the API and as an option additional core material or other additives are delivered. The melt and API or API dispersion is then transferred though a mixing section of the extruder and then delivered to either the spin disc or to a pressurized atomizer unit.

Conventional Pan System

The standard coating pan system consists of a circular metal pan mounted sat an angle on a stand, the pan is rotated on its horizontal axis by a motor, the hot air is directed into the pan and onto the bed surface, and is exhausted by means of ducts positioned through the front of the pan. Coating solutions are applied by spraying the material on the bed surface. As coating is applied the coating solution is dried off. It is common to dust powder mixtures onto wetted beads and dry the beads in layers. A final color and seal coating is often applied.

The Perforated Coating Pan

Coating pan has perforations along its cylindrical portion. It is driven by a variable speed drive. Supply of hot air and exhaust of drying air are arranged to facilitate the coating system through stainless steel plenums positioned on both sides of the perforated coating pan. The pan is enclosed in an airtight housing provided with a suitable door and front glass window. This housing of pan with drive is a stainless steel cabinet accommodating the gearbox, AC variable drive, power panel, hot air unit, exhaust unit and an air fitter.

Liquid spray system is complete with stainless steel liquid storage vessel, variable flow-rate liquid dosing pump, automatic spray gun, and inter-connecting flexible hoses.

The Fluidized Bed Coater

The Fluid Bed Technology is the more modern approach to coating beads. It is a very efficient coating technique. The major advantage of the Fluid Bed Systems it is a closed system that air suspends the beads.

In a fluidized bed a coat is introduced to cover the core particles inside the bed. In the process, a layer is deposited onto the surface of fluidized solid particles by spraying with a solution of the coating material. The fluidizing gas is also use to dry the deposited solution. There is considerable diversity in methods of using fluidized bed technology. For e.g. liquids can be applied to fluidized particles in a variety of ways, including top, bottom and tangential spraying. For a given product, each method can offer markedly different finished product characteristics.

Fluidized beds are used for coating because of their high energy and mass transfer. Fluidized beds for film coating can be divided into three groups: top spray, tangential spray, and bottom-spray equipment.

In the top spray bed, the expansion chamber is lengthened to allow powder to remain fluidized longer and to move with a higher velocity, so that agglomeration is minimized. The expansion chamber is conically shaped to allow uniform deceleration of air stream. The filter housing is larger and designed to shake the fines back into the bed interrupting fluidization; this reduces agglomeration tendencies. The nozzle is positioned low in the expansion chamber so that coating material impinge on the fluidized particle a short distance from the nozzle; this reduces droplet spray drying and provides for longer subsequent drying of the coated particles. The top spray coater has been used to apply aqueous and organic solvent based film coatings, controlled release coatings. Smaller microspheres in this technique would allow smaller final beads and/or thicker coatings.

In the bottom spray coating, the Wurster machine employs a cylindrical product container with a perforated plate. Inside the container is a second cylinder (coating partition) with is raised slightly above the perforated plate, centered in the plate below this partition is a spray nozzle used to dispense the coating solution. The perforated plated is designed with large holes in the area under the coating partition and smaller holes in the remainder of the plate, except for one ring of large holes at the perimeter. The design allows the core particles to be pneumatically transported upward through the coating partition, and downward outside this partition. Material passing through coating partition receives a layer of coating material, dries in the expansion chamber, and falls back in a semi fluidized state. Material circulates rapidly in this fashion and receives layer of coating material, dries in the expansion chamber, and falls back in a semi fluidized state material circulates rapidly in this fashion and receives a layer of coating on each pass through the coating partition. The ring of large holes on the periphery of perforated plate prevents the accumulation of material at the container wall. It is used for coating small particles, beads, tablets and capsules.

The tangential spraying system, which is commonly fitted with a rotating bottom plate, can achieve film quantities nearly as good as the bottom spraying system. The rotation of the plate nicely supports product movement, so that the required air amount is mainly used for drying process and only to a smaller degree for the product movement.

Fluid Bed Coating

For microspheres of small sizes the coating film is used to control the release rate of the API. Microspheres allow the loading of the API in a coating layer first up to 1 to 2 mm in diameter followed by the application of the release controlling layer. Thus the small particle diameter of the microsphere add to API loading capacity and the decreasing particle diameter and thus the specific surface area of a substrate increase dramatically and the required coating weight gain is not experienced. Drug layering can be applied more rapidly than the final controlled coating layer.

Rotating Disk Granulation

Granulation techniques utilizing centrifugal fluidizing disk that can be moved up or down to create a variable slit opening between the outer perimeter of the disk and the sidewall of the container. Air is drawn into the product container through the slit under negative pressure. This fluidizes the material along the circumferential surface of the product container. At the same time the disk rotates at varying speeds and moves the product by the centrifugal force to the outer portions where it is lifted by the fluidizing air stream into the expansion chamber. As the material decelerates, it descends to the center of the disk and repeats the same sequence. The fluidization pattern is often described as a spiraling helix or rope-like pattern around the inside of the rotor chamber.

Spray nozzles can be immersed in the bed of fluidized material and spray applied in tangential fashion with respect to the particle flow. Microspheres in this process allows for a starting controlled surface onto which the coating powder with API can be layered onto and held by a spray solution of coating materials in a rapid layering application approach. Based on the uniformity of both shape and size these microspheres allow for a uniform and rapid gain in weight and maintain separation readily versus standard crystal seeds currently used and starter material.

Dosage Forms

The various embodiments of the composition, according to the present invention, may be used in a variety of dosage forms including, but not limited to, chewable tablets, swallow tablets, soft chews including tablets and soft gel capsules, orally disintegrating tablets, orally dispersible powders, mini-tablets, lozenges, film strips, gums, gels, ointments and creams, tablet inserts (eye, ear, vaginal), suppositories, hard shell capsules, liquid fill capsules, liquid suspensions and sustained release beads.

In some embodiments, the dosage form may include a pharmaceutically acceptable ingredient including excipients, diluents; disintegrants; binders; fillers; bulking agent; organic acid(s); colorants; stabilizers; preservatives; lubricants; glidants/anti-adherants; chelating agents; vehicles; bulking agents; stabilizers; preservatives; tonicity adjusting agents; local anesthetics; pH adjusting agents; antioxidants; osmotic agents; chelating agents; viscosifying agents; wetting agents; emulsifying agents; acids; sugar alcohol; reducing sugars; non-reducing sugars and the like used either alone or in combination thereof. In some embodiments, the pharmaceutically acceptable ingredients may include excipients, binders, lubricants, sugar alcohols, disintegrating agents, colors, flavors and the like used either alone or combinations thereof.

In some embodiments, the composition may be used in a directly compressible dosage form. The term "directly compressible" means that the composition can be compressed to tablet form on standard tableting machines (including, but not limited to high speed tableting machines) using standard (i.e., without any specially machined, shaped or coated surfaces) punches and dies, without any significant amount of the composition adhering to the punches and dies by applying compressive pressure to the composition. In some embodiments, the compression pressure ranges from 60 MPa to 170 MP. In some embodiments, the compression force ranges from 80 MPa to 150 MPa. In some embodiments, the compression pressure is at least 60 MPa.

The term "pharmaceutical formulation" as used herein refers to formulations containing the composition of the present invention in combination with carriers or excipients suited to a selected drug delivery platform, e.g., a capsule, an orally dispersible formulation, an effervescent formulation, a chewable tablet, a lozenge, a hard or swallow tablet, or the like.

"Carriers" or "vehicles" as used herein refer to carrier materials suitable for oral drug administration, and include any such materials known in the art, e.g., diluents, binders, granulating agents, disintegrants, lubricating agents, colorants, flavoring agents, and the like.

Various types of pharmaceutical formulations may be prepared using the presently disclosed microspheres and compositions, including powders, chewable tablets, orally dissolving tablets, effervescent formulations, and liquid dispersions. For solid formulations such as powders, chewable tablets, orally dissolving tablets and effervescent formulations, conventional carriers, excipients and additives can be employed, including diluents, binders, granulating agents, disintegrants, flavoring additives, and the like. Examples of the normally employed excipients include pharmaceutical grades of mannitol, lactose, starch, and the like. Liquid pharmaceutical compositions containing the present microspheres will generally be prepared by dispersing or suspending the microcapsules in a non-aqueous carrier which does not cause release of the drug, or else by dispersing the microspheres or composition in an aqueous carrier immediately prior to administration to the patient. For example, the microspheres or composition may be provided as a free-flowing particulate material, as in a sachet or other suitable package, and such a particulate material may be dispersed in an aqueous carrier. These solid or liquid formulations may contain any amount of the microsphere or composition needed to provide the desired amount of the active ingredient contained in the microsphere or composition. For example, amounts of microspheres or composition on the order of about 10 wt. % to about 95 wt. % of the dosage form may be used. Actual methods of preparing such dosage forms are known, or will be apparent, to those skilled in this art.

It will be apparent to one of skill in the art that various modifications and variations can be made in the methods and compositions of the present invention without departing from the spirit or scope of the invention. Thus, it is intended that the present invention cover the modifications and variations of the present invention provided they come within the scope of the appended claims and their equivalents.

EXAMPLES

The following examples are given to illustrate the present invention. It should be understood, however, that the invention is not to be limited to the specific conditions or details described in these examples. Throughout the specification, any and all referenced publicly available documents, including but not limited to a U.S. patent, are specifically incorporated by reference.

Example 1

Mannitol (EP) (Shandong Tianli Pharmaceutical Ltd., Guangzhou, China) and mannitol/sorbitol (2.3%) (sorbitol, Roquette, Keokuk, Iowa) microspheres were produced by prilling (spray chilling) of a melt of the polyols in a stainless steel 2 quart sauce pan. The melted polyol was poured into a heated pressure vessel that was heated by electrical heat bands. The heated pressure vessel was pressurized to 50 psig and the plug valve at the bottom of the vessel was opened to send the mannitol thru the spray line to the nozzle. The spray line was heated by electrical heat tape. The nozzle was heated with a propane torch prior to opening the valve. The prills from the nozzle (Spraying Systems 6501) were collected on plastic and bagged for evaluation. Microspheres particle size distribution was determined by Malvern Mastersizer Laser analysis (Malvern, Pa.). Table 1 shows the particle size distribution of the microspheres. Microsphere diameters were in the 250 µm mean range with a broad distribution (d(0.1)=124 and d(0.9)=473 um or 473/124=3.8 to 1 distribution ratio and d(0.1)=204 and d(0.9)=598 um or 598/204=2.9 to 1 distribution ratio. FIG. 1 shows a photomicrograph of the microspheres demonstrating a total smooth glass-like surface of the microspheres. (Carl Zeiss Microscope Model Axio Vert.A1 (Oberkochen, Germany)).

TABLE 1

| Particle size distribution | | | | |
|---|---|---|---|---|
| Sample | d(0.1) | d(0.5) | D(0.9) | PSD Ratio |
| Sample 1 (Mannitol) | 124 | 250.6 | 473 | 3.8 |
| Sample 2 (Mannitol) | 122 | 261.6 | 494 | 4.0 |
| Sample 3 (Mannitol/Sorbitol) | 164 | 323 | 567 | 3.45 |
| Sample 4 (Mannitol/Sorbitol) | 96 | 225 | 451 | 4.7 |

Example 2

Mannitol EP (Shandong Tianli Pharmaceutical Ltd., Guangzhou, China), mannitol/sorbitol (2.3%) (sorbitol, Roquette, Keokuk, Iowa) and mannitol/polysorbate 80 (Unichema, New Castle, Del.) microspheres were made by melting polyol and dropping melt to spin disc for formation of microspheres. Mannitol is melted in pan or oven at 10° C. above its melting point for mannitol a temperature higher than 176° C. Once melted, the liquid mannitol is spun into a stream which, by centrifugal force, is spread into a thin film and exits the disk as a ligament that breaks into droplets or exits as droplets. Surface spinner style disk is preferred with a diameter of 4 inches or more and speed capabilities of from 500 RPM to 11,000 RPM. Wheel RPM controls film thickness and thus droplet/bead size. Microspheres are allowed to fall at least 8 feet in room temperature or chilled air to congeal. Once congealed a coarse screen can be used to complete cooling and maintain separation. Any twinning or chill damaged microspheres are removed with a bead shape shorter.

Microspheres were analyzed for particle size using Malvern Mastersizer. Table 2 shows the particle size distribution (PSD) of the microspheres.

Figure 2:
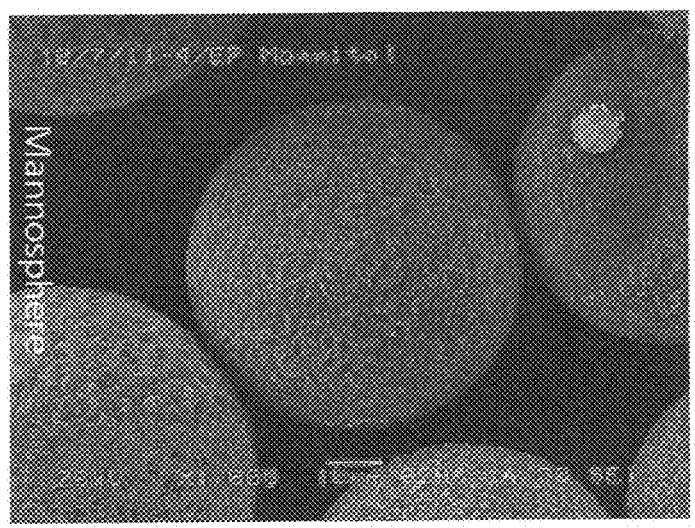
FIG. 2 is a SEM photomicrograph (1000×) of exemplary mannitol microspheres of the present invention.
Figure 3:
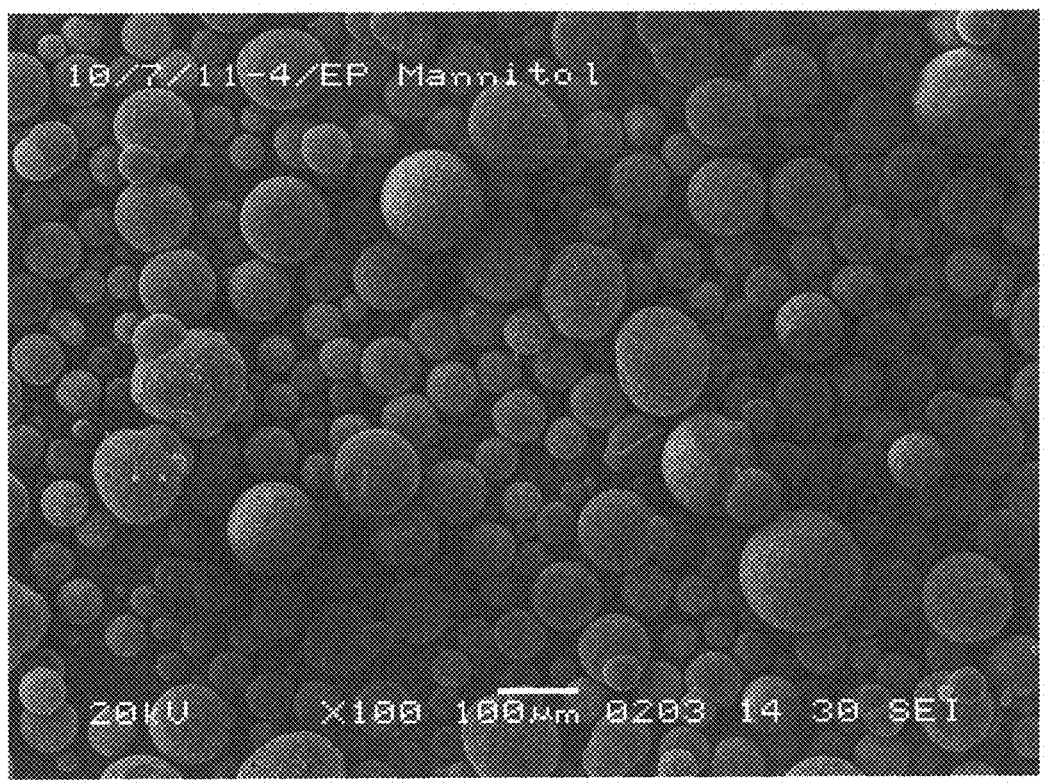
FIG. 3 is a micrograph of SEM of exemplary mannitol microspheres of the present invention.

Scanning electron microscopy (SEM) was performed on exemplary mannitol microspheres. FIG. 2 is a close up micrograph of SEM of the mannitol microspheres made by this process. Note the surface crystal deposited microsteps present, the perfect circularity and the lack of crevices and risers. FIG. 3 is a micrograph of SEM, which shows the size distribution of mannitol microspheres available with this process and the ability to achieve microspheres at sizes down to 10 μm and smaller. Note in this figure the uniformity of shape and circularity/sphericalness even at and down to the 10 μm level.

TABLE 2

Particle size distribution

| Sample | d(0.1) | d(0.5) | D(0.9) | PSD Ratio |
|---|---|---|---|---|
| Run 1-Mannitol EP | 133.6 | 211.7 | 297.2 | 2.2 |
| | Disc Speed: 2000 RPM | | Flow Rate: 110 gm/min | |
| Run 2-Mannitol EP | 120 | 223 | 395 | 3.3 |
| | Disc Speed: 1500 RPM | | Flow Rate: 110 gm/min | |
| Run 3-Mannitol EP | 126 | 216 | 354 | 2.8 |
| | Disc Speed: 1250 RPM | | Flow Rate: 110 gm/min | |
| Run 4-Mannitol EP | 162 | 273 | 456 | 2.8 |
| | Disc Speed: 1000 RPM | | Flow Rate: 110 gm/min | |
| Run 5-Mannitol EP | 226 | 407 | 672 | 2.97 |
| | Disc Speed: 750 RPM | | Flow Rate: 110 gm/min | |
| Run 6-Mannitol EP | 299 | 499 | 777 | 2.6 |
| | Disc Speed: 2000 RPM | | Flow Rate: 49 gm/min | |
| Run 7-Mannitol EP | | | | |
| | Disc Speed: 1500 RPM | | Flow Rate: 49 gm/min | |
| Run 8-Mannitol EP | 178 | 303 | 494 | 2.8 |
| | Disc Speed: 1250 RPM | | Flow Rate: 49 gm/min | |
| Run 9-Mannitol EP | 221 | 373 | 602 | 2.7 |
| | Disc Speed: 1500 RPM | | Flow Rate: 110 gm/min | |
| Run 10-Mannitol EP | 146 | 299 | 531 | 3.6 |
| | Disc Speed: 1500 RPM | | Flow Rate: 49 gm/min | |
| Run 11-Mannitol EP | 178 | 303 | 494 | 2.8 |
| | Disc Speed: 1500 RPM | | Flow Rate: 110 gm/min | |
| Run 12-Mannitol EP | 248 | 447 | 730 | 2.9 |
| | Disc Speed: 1500 RPM | | Flow Rate: 49 gm/min | |
| Run 13-Mannitol EP | 162 | 277 | 469 | 3.1 |
| | Disc Speed: 1500 RPM | | Flow Rate: 200 gm/min | |
| Run 14-Mannitol EP | 127 | 252 | 478 | 3.8 |
| | Disc Speed: 1500 RPM | | Flow Rate: 163 gm/min | |
| | 150 | 310 | 564 | 3.76 |
| Run 1-Mannitol EP (10/7) | Disc Speed: 11000 RPM | | Flow Rate: 110 gm/min | |
| | 29 | 57 | 105 | 3.6 |
| Run 2-Mannitol EP (10/7) | Disc Speed: 11000 RPM | | Flow Rate: 163 gm/min | |
| | 27 | 58 | 117 | 4.3 |
| Run 3-Mannitol EP (10/7) | Disc Speed: 11000 RPM | | Flow Rate: 200 gm/min | |
| | 29 | 63 | 123 | 4.24 |
| Run 4-Mannitol EP (10/7) | Disc Speed: 5000 RPM | | Flow Rate: 200 gm/min | |
| | 33 | 66 | 129 | 3.9 |

TABLE 2-continued

Particle size distribution

| Sample | d(0.1) | d(0.5) | D(0.9) | PSD Ratio |
|---|---|---|---|---|
| Run 5-Mannitol/ Sorbitol | Disc Speed: 5000 RPM | | Flow Rate: 200 gm/min | |
| | 35 | 74 | 138 | 3.9 |
| Run 6-Mannitol/ Sorbitol | Disc Speed: 11000 RPM | | Flow Rate: 300 gm/min | |
| | 24 | 62 | 130 | 5.4 |
| Run 7-Mannitol w/ polysorbate 80 | Disc Speed: 5000 RPM | | Flow Rate: 200 gm/min | |
| | 35 | 74 | 138 | 2.5 |

Karl Fisher Moisture (USP)

Approximately 1.0 g of the mannitol EP microspheres, Colorcon SURESPHERES® sugar/starch spheres (Colorcon, West Point, Pa.), and Werner PHARM-A-SPHERE™ Neutral Pellets (Hanns G. Werner GmbH, Tornesch, Germany) were analyzed for moisture content using in the Karl Fisher method described in US Pharmacopeia (USP) 26. Table 3 shows the moisture content of the mannitol microspheres, SURESPHERES®, and PHARM-A-SPHERE™ Neutral Pellets.

TABLE 3

Moisture content of mannitol microsphere vs. commercial beads

| Product | Mass (g) | Titrant (ml) | Water (%) |
|---|---|---|---|
| SURESPHERES ® | 1.0053 | 2.560 | 1.32 |
| PHARM-A-SPHERE ™ Neutral Pellets | 1.0032 | 1.578 | 0.81 |
| Mannitol (USP) Microspheres (10/7/1-6) | 0.9988 | 0.184 | 0.1 |
| Mannitol (EP) Microspheres (10-6-9) | 1.0087 | 0.036 | 0.02 |

Figure 4:
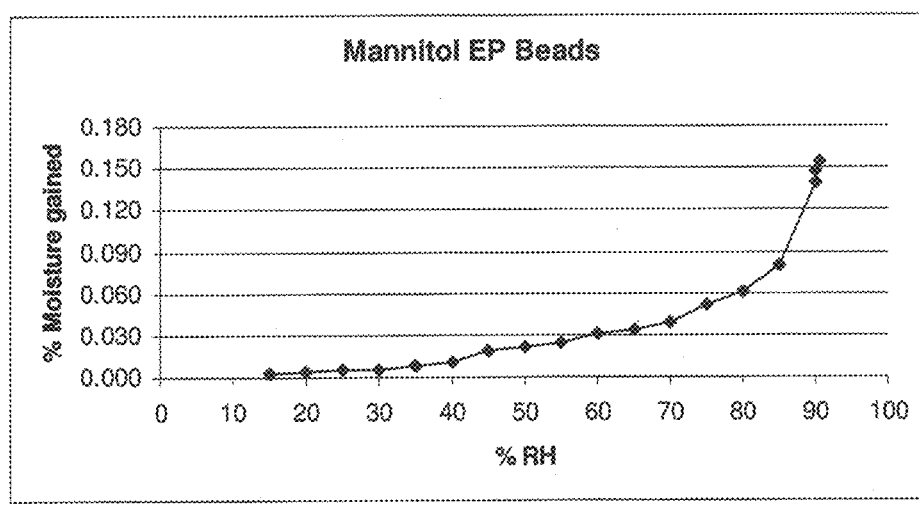
FIG. 4 is a graph illustrating the moisture content of exemplary mannitol microspheres of the present invention.

Dynamic Vapor Sorption 0.2 g of the mannitol EP microsphere was analyzed on an AquaDyne Instrument of the Quantachrome (Quantachrome Instruments Palm Beach Fla.) using the aquaWin—Data Acquisition and Reduction to measure dynamic vapor sorption. FIG. 4 shows the hygroscopicity of mannitol microspheres. Results show that mannitol microspheres are extremely non-hygroscopic at normal process conditions of 60% relative humidity (RH) as weight gain is less than 0.05%. Results also show a lack of moisture adsorbing pore sizes as beads even at 90% RH gained less than 0.2% moisture.

In order to compare the hygroscopicity of the mannitol microspheres to other forms of mannitol, powdered (MANNOGEM® powder, Lot #121101399F, SPI Pharma, Inc.; Pearlitol 50C, Lot # KVKRN, Roquette Freres), granular (MANNOGEM® granular, Lot #121101116G, SPI Pharma, Inc.; Pearlitol 400DC, Lot # E592J, Roquette Freres), and sprayed-dried mannitol (MANNOGEM® EZ, Lot #121101324, SPI Pharma, Inc.; Pearlitol 200 SD, Lot # E983G, Roquette Freres) products were submitted to Quantachrome for Dynamic Vapor Sorption (DVS) analysis.

Figure 5:
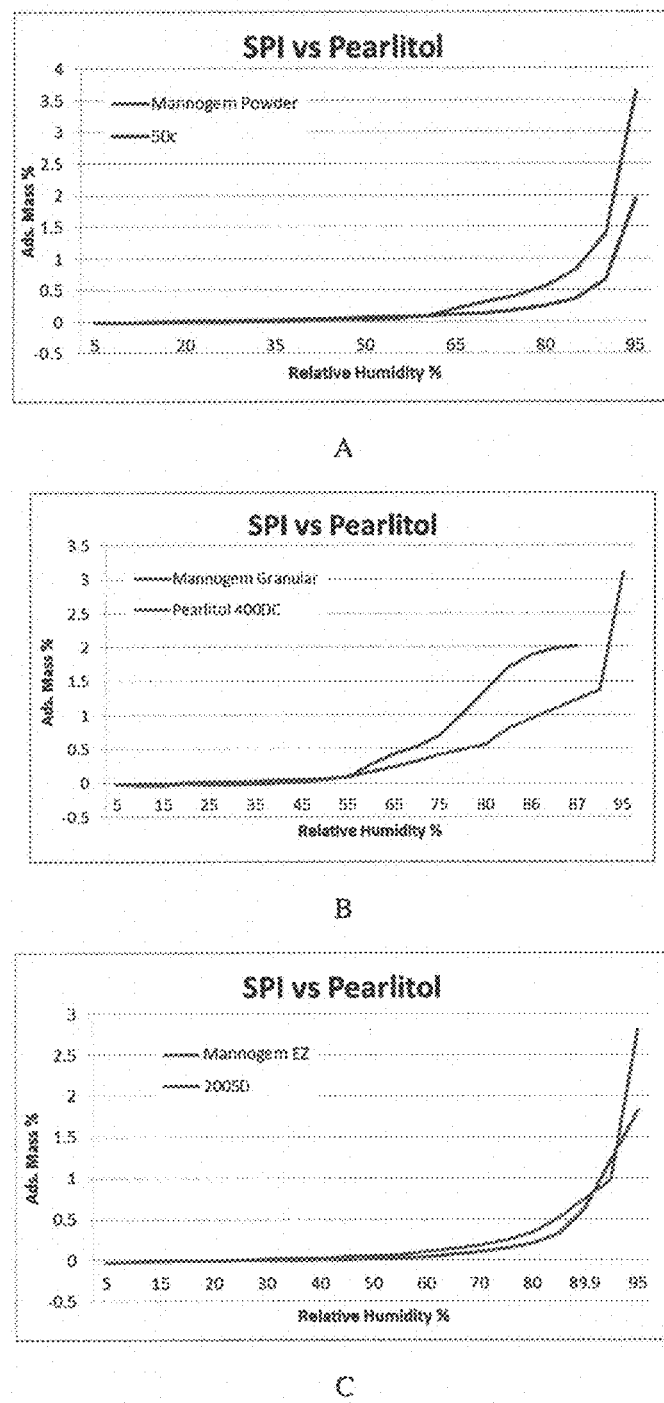
FIG. 5 (A, B and C) are graphs illustrating the moisture content of powdered, granular and spray-dried mannitols.

The adsorption profiles for MANNOGEM® powder and Pearlitol 50c are compared in FIG. 5A. The profile for MANNOGEM® powder shows that it begins to adsorb more moisture at around 62% relative humidity. In addition, the MANNOGEM® powder reaches a higher adsorption at 95% RH.

The adsorption profiles for MANNOGEM® granular and Pearlitol 400DC are compared in FIG. 5B. Similar to the MANNOGEM® powder profile, the MANNOGEM® granular shows a higher moisture adsorption at around 55% relative humidity. The MANNOGEM® granular appears to stop adsorbing moisture at around 86% RH.

The adsorption profiles for MANNOGEM® spray dried and Pearlitol 200SD are compared in FIG. 5C. The profile for MANNOGEM® spray dried shows that the SPI product has a much lower adsorption than the Pearlitol 200SD. The Pearlitol increases in adsorption at around 60% relative humidity. In addition, the Pearlitol 200SD has a much higher adsorption at the highest RH values.

None of the above adsorption profiles for the powder, granular and spray-dried mannitol-based commercial products are below 0.2% moisture content at 95% RH. As seen in FIG. 4, the mannitol microspheres of the present invention have a less than 0.2% moisture weight gain at 95% RH compared to over 1.5% for the MANNOGEM® EZ which was the best performer amongst powder, granular and spray dried products tested.

Figure 6:
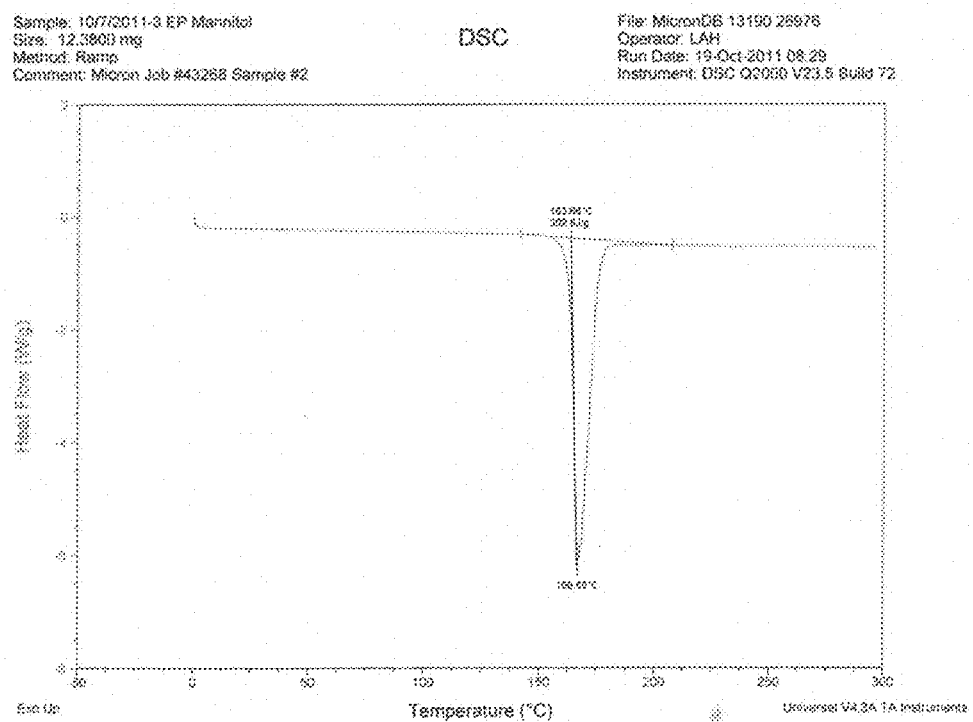
FIG. 6 is a DSC scan of exemplary mannitol microspheres of the present invention.

Mannitol microspheres was measured by differential scanning calorimetry (DSC) using a Thermal Analysis (New Castel, Del.) DSC Q2000 instrument with a version V23.5 data acquisition system at 10° C. per minute from room temperature to 300° C. FIG. 6 shows DSC scan of mannitol microsphere at alpha mannitol melt point of 166° C. and with heat of fusion at 302 J/gm. From Burger*, alpha mannitol heat of fusion is 285.3 J/gm. Thus bond energy/gm is equal to or more than alpha mannitol. Beta is 293 J/gm as reported by Burger*. This demonstrates that the bond energy in the crystal lattice is equal to or less than that of the microsphere and thus the bead is 100% crystalline with limited to no amorphous regions.

Skeletal Density

Mannitol EP microspheres were analyzed for skeletal density using an Ultrapyc 1200e V4.02 of Quantachrome Corporation (Palm Beach, Fla.). Table 4 shows skeletal density of mannitol microspheres.

TABLE 4

Density of mannitol microspheres by helium pycnometry

| Run | Volume (cc) | Density (g/cc) |
| --- | --- | --- |
| 1 | 0.8655 | 1.4651 |
| 2 | 0.8674 | 1.4620 |
| 3 | 0.8674 | 1.4620 |
| 4 | 0.8680 | 1.4609 |
| 5 | 0.8684 | 1.4602 |
| 6 | 0.8692 | 1.4590 |
| 7 | 0.8688 | 1.4595 |

Derivation Achieved: 0.0291%; Average volume: 0.8688 cc; Volume Std. Dev.: 0.0003 cc; Average Density: 1.4596 g/cc; Density Std. Dev.: 0.0005 g/cc; Coefficient of Variation: 0.0342%

The closeness of the helium pycnometry skeletal density to the true density of alpha mannitol at 1.468 gm/cm$^{-3}$ (Burger et al.*) versus 1.4590 to 1.4651 for samples indicates microspheres are solid structures and substantially lack interior voids/porosity.

| Mannitol Crystalline Density | Beta | Alpha |
| --- | --- | --- |
| Density gm/cm$^{-3}$ | 1.49 | 1.468 |

*Artur Burger, Jan-Olav Henck, Silvia Hetz, Judith Rollinger, Andrea Weissnicht, Hemma Stottner. *Journal of Pharmaceutical Science* 89.4 (2000): 457-468.

Figure 7:
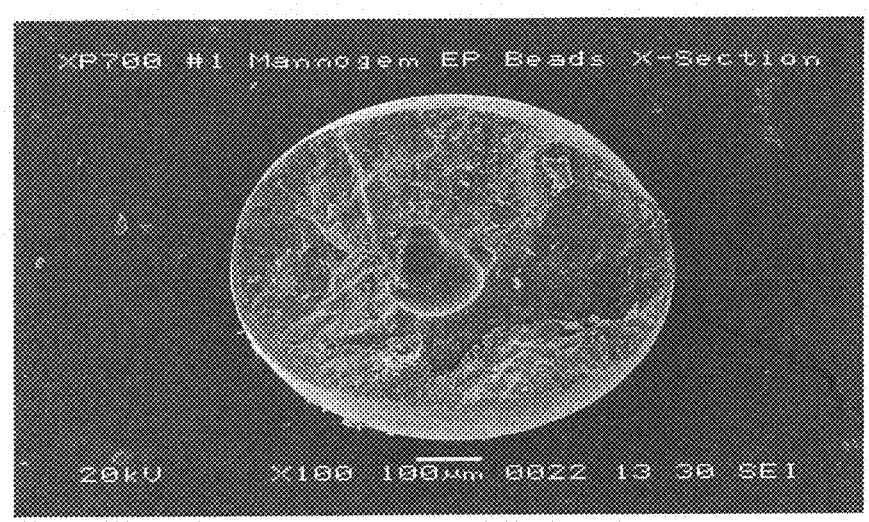
FIG. 7 is a micrograph of SEM of sectioned exemplary mannitol microsphere of the present invention.
Figure 8:
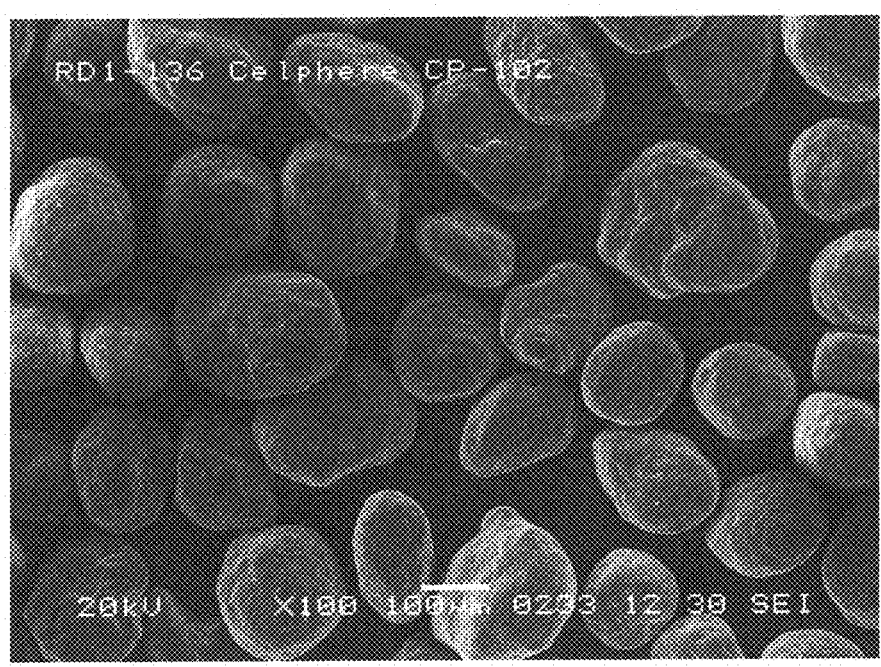
FIG. 8 is a micrograph of SEM of Celphere CP-102 microcrystalline cellulose beads (Asahi Kasei Corporation, Tokyo, Japan).
Figure 9:
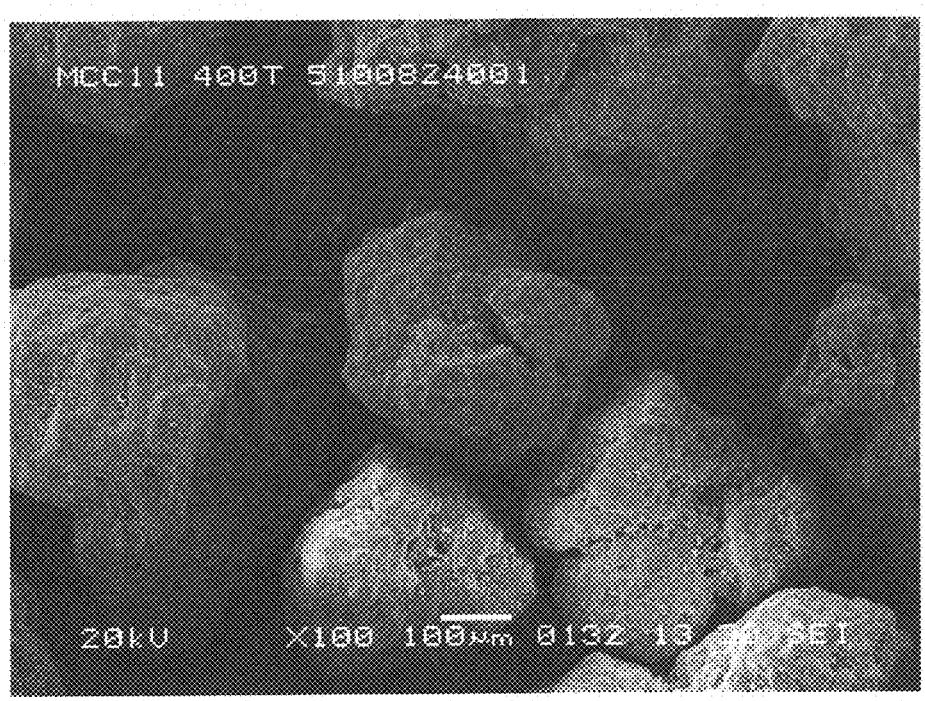
FIG. 9 is a micrograph of SEM of MCell 400 mannitol beads (Pharmatrans Sanaq AG, Allschwil, Switzerland).
Figure 10:
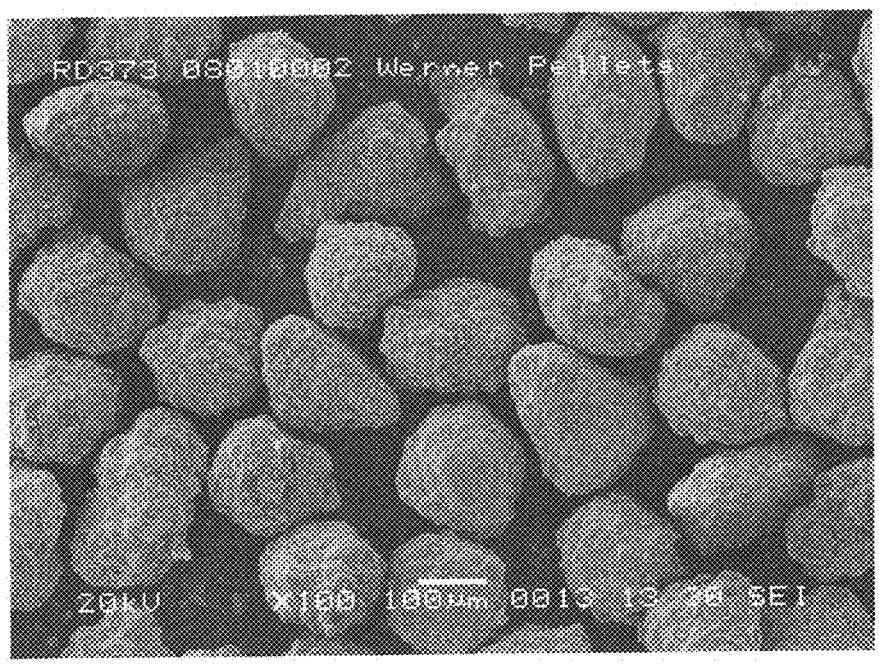
FIG. 10 is a micrograph of SEM of PHARM-A-SPHERE™ Neutral Pellets (Hanns G. Werner GmbH, Tornesch, Germany).
Figure 11:
FIG. 11 is a micrograph of SEM of SURESPHERES® sugar/starch spheres (Colorcon, West Point, Pa.).

Scanning electron microscopy (SEM) was performed on a sectioned mannitol microsphere to examine the interior structure of microsphere. FIG. 7 is a micrograph of the SEM showing that the mannitol microsphere is solid and lacks interior voids. SEM was also performed on current commercial microspheres/beads: Celphere CP-102 microcrystalline cellulose beads (Asahi Kasei Corporation, Tokyo, Japan), MCell 400 mannitol beads (Pharmatrans Sanaq AG, Allschwil, Switzerland), PHARM-A-SPHERE™ Neutral Pellets (Hanns G. Werner GmbH, Tornesch, Germany), SURESPHERES® sugar/starch spheres (Colorcon, West Point, Pa.). FIG. 8 is a micrograph of SEM of Celphere CP-102 microcrystalline cellulose beads, which have a smooth polymer type surface with some risers and convexed indentations present but limited cracks and fissures. The common watermelon or potato shape is apparent which would cause these particles to wabble in flow versus roll and also then to segregate on a shape basis. FIG. 9 is a micrograph of SEM of MCell 400 mannitol beads, which shows the imperfect spherical nature of the beads, as well as the presence of convexity and lack of solidity caused by very deep fissures and risers. Also the bead structure is a fusion of multiple particles in a granular form verses a singular crystal body. FIG. 10 is a micrograph of SEM of PHARM-A-SPHERE™ neutral pellets, which shows a lack of the deep crevices seen in the MCell beads but shows what appears to be a single grown particle without appearance of agglomeration. FIG. 11 is a micrograph of SEM of SURESPHERES®, which shows a non-spherical appearance, solid body and a lack of crevices.

Circularity

Figure 12:
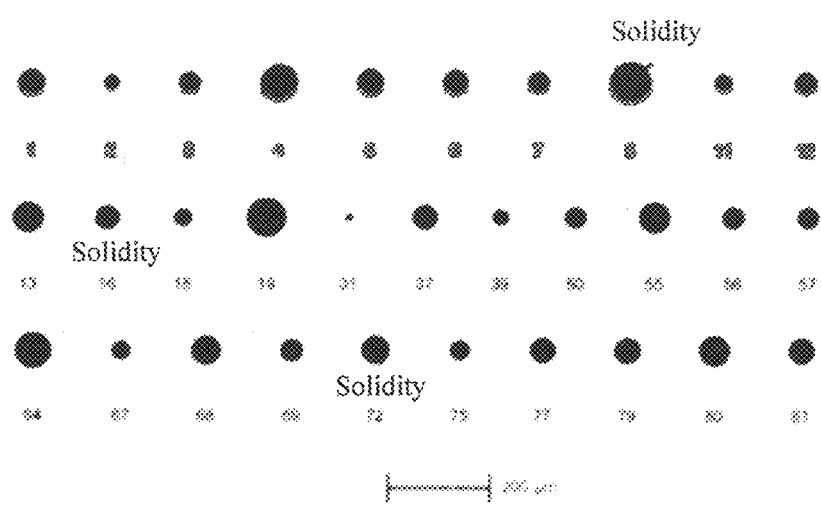
FIG. 12 is an image of exemplary mannitol microspheres of the present invention.
Figure 13:
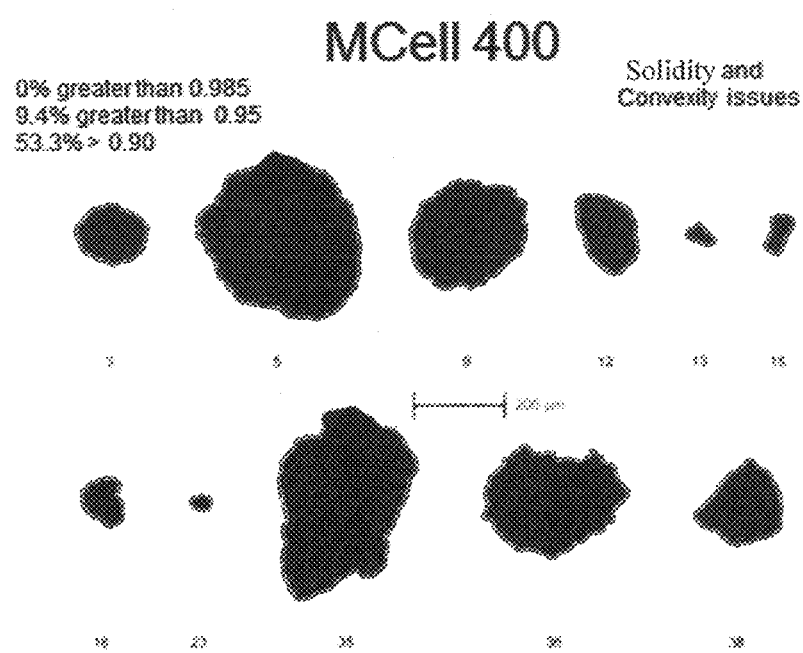
FIG. 13 is an image of MCell 400 mannitol beads (Pharmatrans Sanaq AG, Allschwil, Switzerland).
Figure 14:
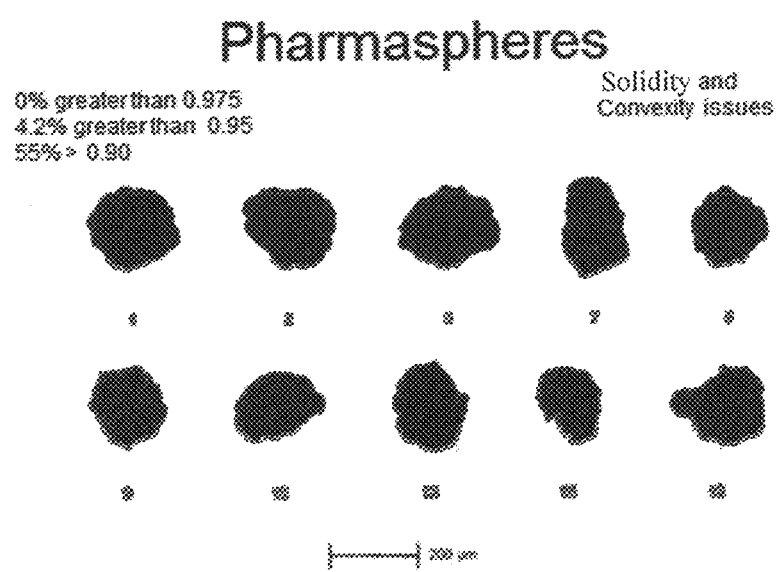
FIG. 14 is an image of PHARM-A-SPHERE™ Neutral Pellets (Hanns G. Werner GmbH, Tornesch, Germany).
Figure 15:
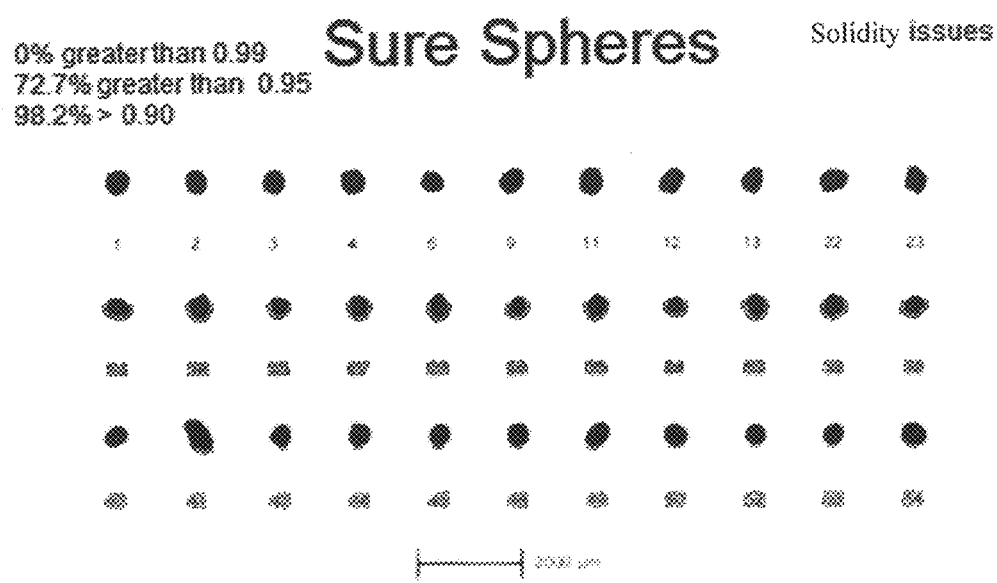
FIG. 15 is an image of SURESPHERES® sugar/starch spheres (Colorcon, West Point, Pa.).
Figure 16:
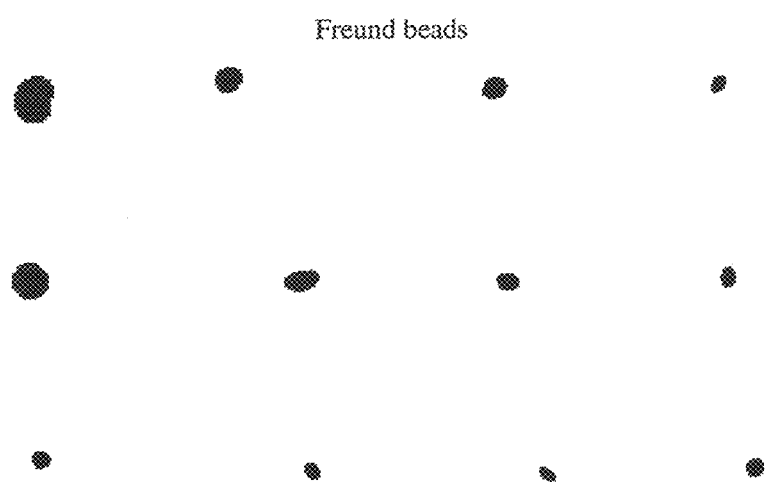
FIG. 16 is an image of Nonpareil-108 mannitol beads (Freund Industrial Co., Ltd., Tokyo, Japan).

Characterization of the sphericity or circularity of microspheres was conducted by Particle Technology Labs (Downers Grove, Ill., USA). Automated microscopy and image analysis techniques (Malvern Morphologi G3S automated particle image analysis system, Malvern Instruments Inc., USA) were used to characterize the morphology of microspheres of the present invention, and to compare to current commercially available microspheres, and to calculate mean circularity, aspect ratio, convexity and solidity of each. FIGS. 12-16 are the images generated for each. The number below the microsphere in the FIG. 12-15 is the random selection of microsphere the instrument used to print the silhouettes. FIG. 12 is an image of exemplary mannitol microspheres of the present invention. Note the only thing seen out of round in the silhouette picture is particles with point appendages/attachments called twinings. These types of twining particles can be prevented or removed after manufacture to create a product of perfect spherical shape. FIG. 13 is an image of MCell 400 mannitol beads (Pharmatrans Sanaq AG, Allschwil, Switzerland), which shows their non-perfect spherical nature, the presence of risers and of convexed surfaces. FIG. 14 is an image of PHARM-A-SPHERE™ Neutral Pellets (Hanns G. Werner GmbH, Tornesch, Germany), which shows they are non-perfect spheres with risers. FIG. 15 is an image of SURESPHERES® sugar/starch spheres (Colorcon, West Point, Pa.), which shows their non-spherical appearance. FIG. 16 is an image of Nonpareil-108 mannitol beads (Freund Industrial Co., Ltd., Tokyo, Japan), which shows they are not spherical and appear to have risers on the surface.

The circularity of each of the various microspheres was determined. Circularity is a measurement of the calculated peripheral length of a circle of the same silhouetted area of a particle's blocking a light source/the particle's actual peripheral length with values in the range from 0-1. A perfect circle has circularity of roundness 1.0, while a needle-shaped object has roundness close to 0. Table 5 shows the circularity of various shapes (Image Analysis: Evaluating Particle Shape by Horiba Particles on Jul. 7, 2011 by Jeff Bodycomb www.horiba.com).

TABLE 5

Circularity of various shapes

| Shape | ● | ■ | ▲ | ▮ | ▏ | ▕ |
|---|---|---|---|---|---|---|
| Circularity | 1.0 | 0.886 | 0.777 | 0.660 | 0.509 | 0.4 |

The circularity—is typically determined using the equation:

$$\text{Circularity} = 2(\pi\ \text{area})^{0.5}/P$$

where A is the measured area and P is the perimeter length of the microspheres. Circularity is calculated in accordance with International Organization for Standardization (ISO) 9276-6 (2008).

Figure 21:
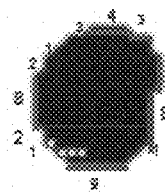
FIG. 21 is a diagram illustrating an example measurement of circularity.

FIG. 21 depicts an example circularity calculation. In this depiction, the 0.886 circularity relates to the shape of a square or in three dimensions a cube and indicates the particle has sharper point or corners in its surface structure and would tumble verses roll. Tumbling is damaging to coating and causes segregation on shape and sharp edges cause issues in both coating stress and coating distribution, resulting in uneven coating thickness and coat cracking. Sharp edges on the bead surface can also break off and become incorporated in the coating and cause cracking and early release issues. Sharp edges can also add stress to the coating as it dries and cause the coating to crack. The presence of cracking can lead to the need to use more plasticizer which causes the coated particle to be tackier. Table 6 shows the circularity of the various microspheres tested.

TABLE 6

Circularity of various microspheres

| Material | Maker | Lot | Circularity % > 0.95 |
|---|---|---|---|
| Mannospheres | SPI Pharma | 10/7/11-4 | 96.8% |
| SURESPHERES ® 20/25 | Colorcon | ST502051 | 72.7% |
| MCell 400 T | Pharmatrans Sanaq AG | 5100824001 | 4.2% |
| PHARM-A-SPHERE ™ | Werner | 08010002 | 9.4% |
| Mannitol Spheres | Freund | | 7.5% |

Figure 17:
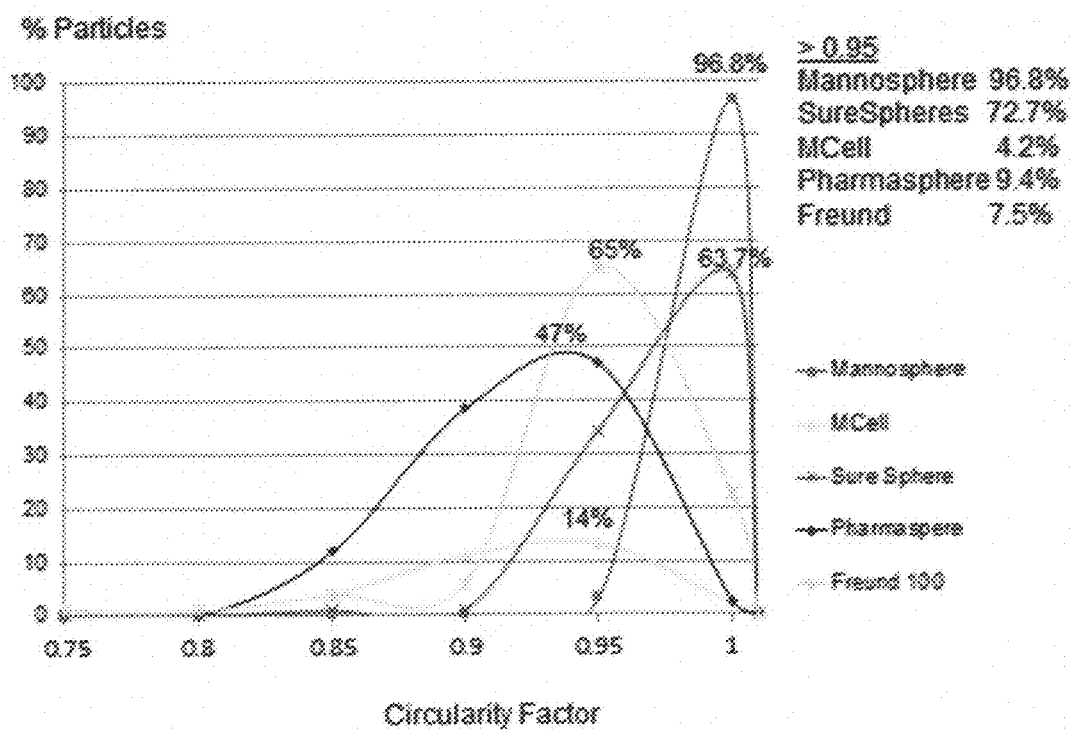
FIG. 17 is a graph illustrating the circularity of exemplary mannitol microspheres of the present invention in comparison with various commercially available microspheres.

FIG. 17 is a graph of the circularity of the various microspheres examined. The results show that >95% of the mannitol microspheres of the present invention (Mannosphere) are perfect circles at greater than a circularity of 0.99, with perfection being >0.995. Also note the difference in distribution between the various commercial materials. The values below 0.9 mixed in with values above 0.95 will lead to a segregation issue based on the fact that some microspheres will tumble while others will roll. The data on circularity demonstrates that 96.8% of the mannitol microspheres of the present invention have a greater than 0.95 circularity rating, while 0% of the MCell microspheres have a circularity of greater than 0.985. Therefore they would be expected to tumble more than roll. Likewise, 0% of the PHARM-A-SPHERE™ have a circularity of greater than 0.975, and therefore they would be expected to tumble and bounce more than roll. Likewise, 0% of the SURESPHERES® have a circularity of greater than 0.99 with 72.7% greater than 0.95, thus some of these beads will roll but some will tumble more than roll.

Aspect Ratio

The aspect ratio of each of the microspheres was also determined. Aspect ratio is defined as the ratio of the length of a sphere divided by the width, with the microspheres being considered circular (spherical) if the aspect ratio lies between 0.95 and 1.00. Table 7 shows the aspect ratios of various shapes (Image Analysis: Evaluating Particle Shape by Horiba Particles on Jul. 7, 2011 by Jeff Bodycomb www.horiba.com). The aspect ratio is sensitive to how isometric the particle is. Particles with a high aspect ratio not only tumble but they tend to lodge in pore spaces in the coating bed and bounce as they tumble. This is a measure of rod, plate or needle-like characteristics of a particle.

TABLE 7

Aspect ratio of various shapes

| Shape | ● | ■ | ▲ | ▮ | ▏ | ▕ |
|---|---|---|---|---|---|---|
| Circularity | 1.0 | 0.886 | 0.777 | 0.660 | 0.509 | 0.4 |
| Aspect Factor | 1.0 | 1.0 | 1.0 | 0.25 | 0.10 | 0.05 |
| Aspect Ratio | 1:1 | 1:1 | 1:1 | 1:4 | 1:10 | 1:20 |

Figure 22:
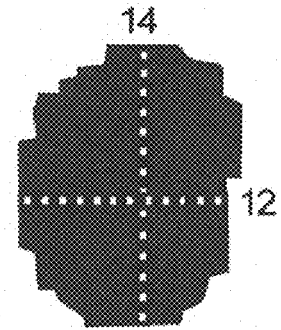
FIG. 22 is a diagram illustrating an example measurement of aspect ratio.
Figure 22:
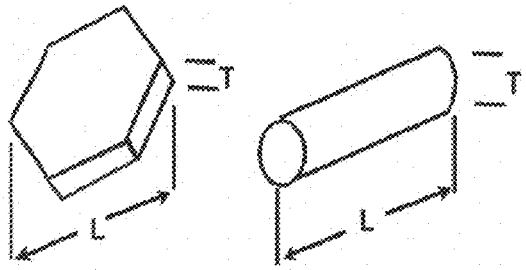
Figure 23:
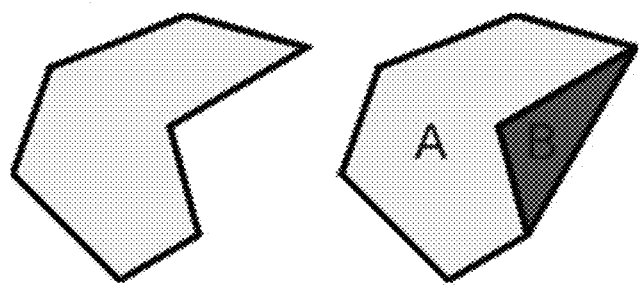
FIG. 23 is a diagram illustrating an example measurement of convexity.
Figure 24:
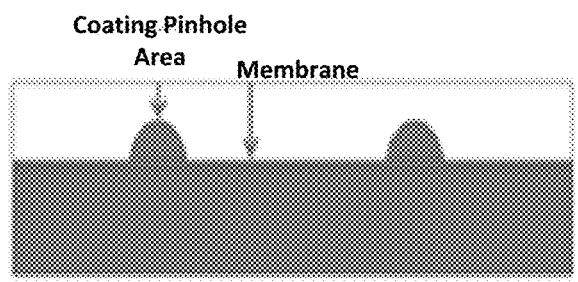
FIG. 24 is a diagram illustrating example coating pinhole area and risers.
Figure 24:
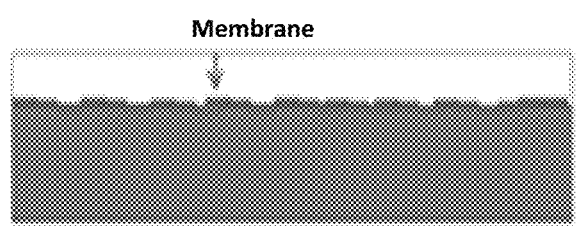
Figure 25:
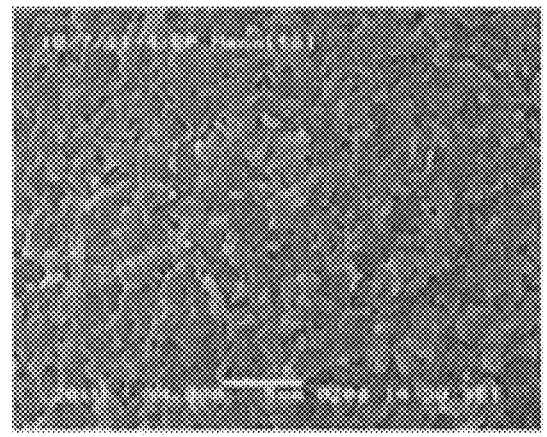
FIG. 25 is a micrograph showing risers on an exemplary mannitol microsphere according to an embodiment of the present invention.

Aspect ratio is the ratio of the shortest diameter of particle to the longest diameter of a particle. Aspect ratio is calculated in accordance with International Organization for Standardization (ISO) 9276-6 (2008). Feret measured diameters as parallel lines brought in to touch particle at any angle. Thus it is the shortest separation of these lines divide by the longest separation. See, e.g., FIG. 22.

Aspect Ratio is peak height but not crevice biased. The closer the aspect ratio is to 1 the more free rolling, less tumbling, mechanically interlocking and bouncing is a particle will it flows during the process of coating.

Figure 18:
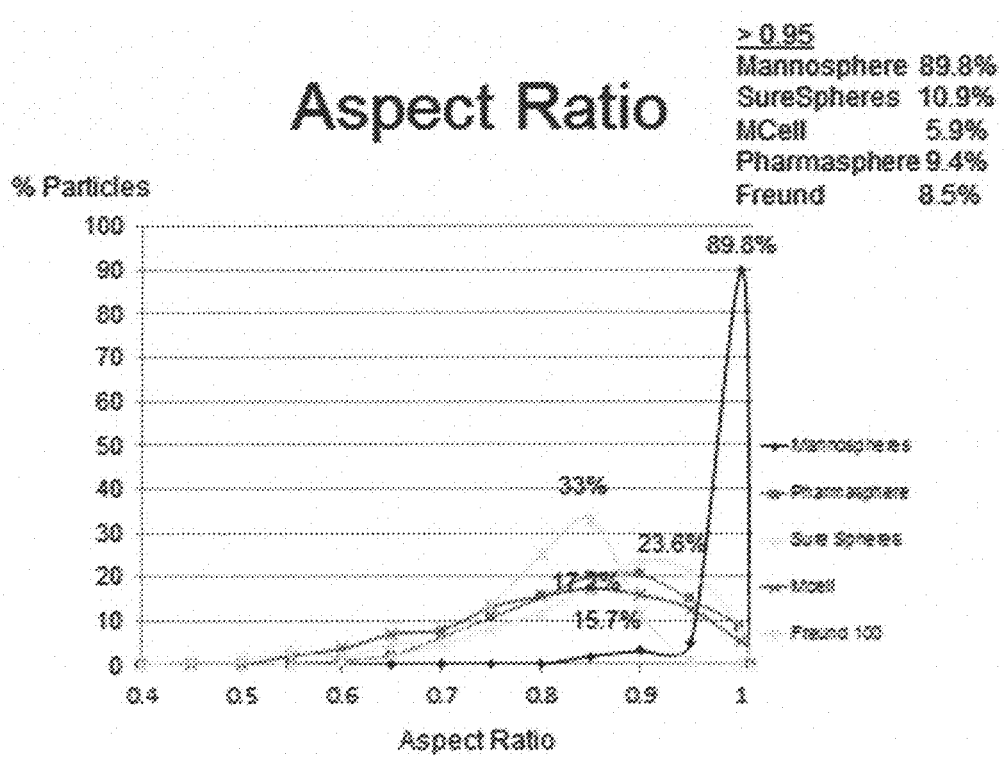
FIG. 18 is a graph illustrating the aspect ratio of exemplary mannitol microspheres of the present invention in comparison with various commercially available microspheres.
Figure 19:
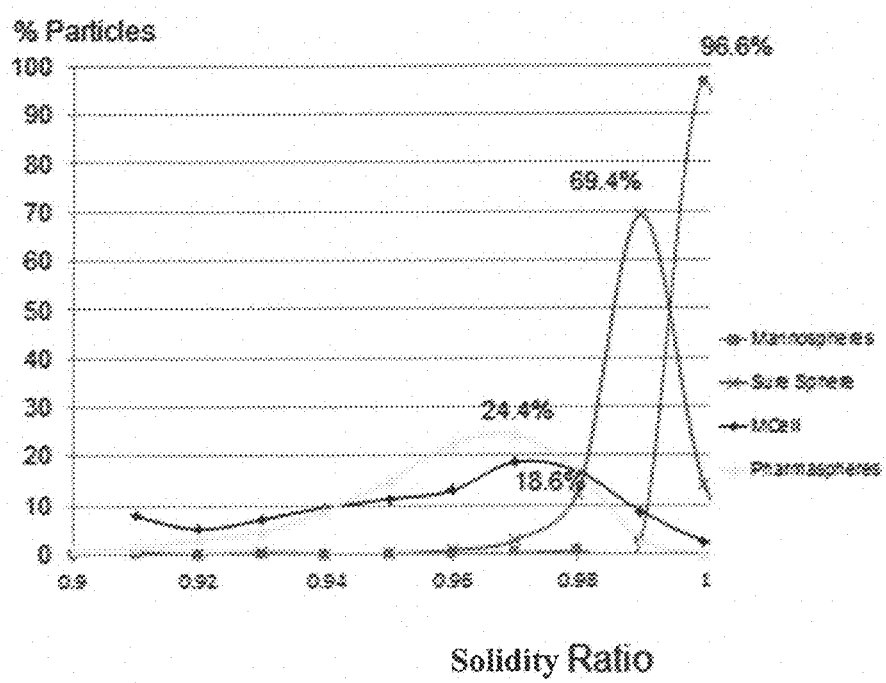
FIG. 19 is a graph illustrating the solidity of exemplary mannitol microspheres of the present invention in comparison with various commercially available microspheres.
Figure 20:
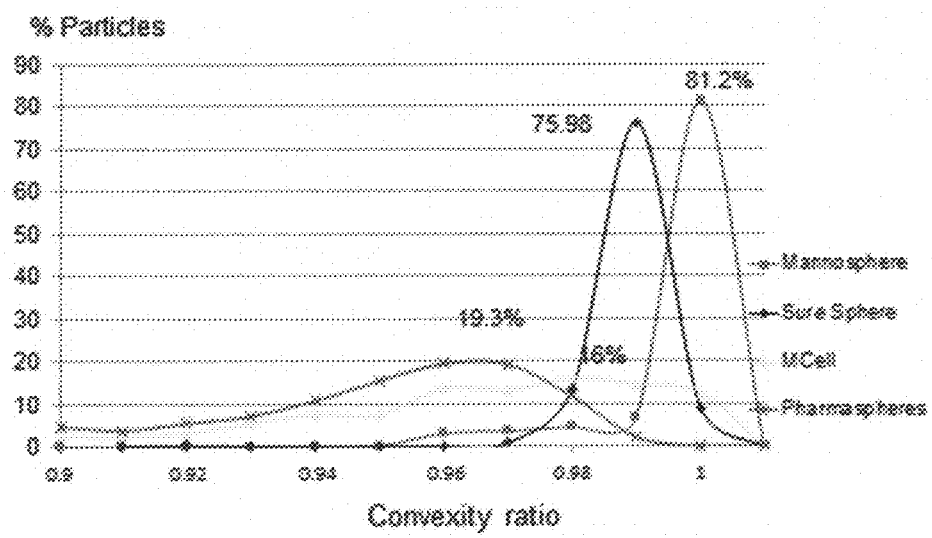
FIG. 20 is a graph illustrating the convexity of exemplary mannitol microspheres of the present invention in comparison with various commercially available microspheres.

Table 8 shows the aspect ratios of the microspheres tested and FIG. 18 is a graph of the aspect ratios of the various microspheres tested. The results show a large disparity between other commercially available beads/microspheres and the microspheres of the present invention. With 89.8% of the microspheres of the present invention (Mannospheres) greater than 0.95 in aspect ratio and all the other beads less than 12% have aspect ratio of greater than 0.95. Also note the distribution of aspect ratios in the samples. Motion patterns change based on aspect ratio thus a narrow distribution of aspect ratio tend to flow the same with less segregating. A broad aspect shape range tends to segregate based on its motion patterns being different. Thus the broader the aspect ratio or factor the greater the segregation risk. Coating uniformity requires control of the surface being coated in the spray pattern called the spray flux, appearance of the microsphere in the area of the spray. Mixing of spherical particles of equal size with other shapes such as watermelon, oblong, flakes, and/or rods will cause changes in flux rate of a microsphere. This can occur by submersion of the particles under the bed below the surface being sprayed on, movement of the particles based on its shape more rapidly/slowly thought the spray zone or movement of the particle based on its shape alone into regions/area where spray is not being applied or applied as fast.

TABLE 8

Aspect ratio of the microspheres tested

| Material | Maker | Lot | Aspect ratio % > 0.95 |
|---|---|---|---|
| Mannospheres | SPI Pharma | 10/7/11-4 | 89.8% |
| SURESPHERES ® 20/25 | Colorcon | ST502051 | 8.2% |
| MCell 400 T | Pharmatrans Sanaq AG | 5100824001 | 5.1% |
| PHARM-A-SPHERE ™ | Werner | 08010002 | 8.47% |
| Mannitol Spheres | Fruend | | 0% |

Solidity

The microspheres of the present invention and current commercial microspheres/beads were examined for solidity. Solidity looks for missing areas caused by risers or indentations in the surface of the microsphere or particle. In order to determine the solidity, a cord is wrapped around the microsphere to approximate the area of the microsphere or particle without convex (indented areas) due to crevices and risers off the surface. The area of the microsphere or particle is exactly measured as the shadow of the image of the microsphere or particle in a light path. The area of the microsphere or particle is then divided by the area inside the cord stretched over the microspheres' or particles' outer surface. Solidity is calculated in accordance with International Organization for Standardization (ISO) 9276-6 (2008).

A sphere has a solidity of 1. A cube, a triangle (pyramid) or a rod would also have a solidity of 1. Although a cube and a pyramid have corners/edges, they do not have surface risers or crevices. Any surface indentations or surface bumps would add to the area inside the cord. Thus solidity as a factor is then related to the area associated with the convexity area of the microsphere as area lost ratio to solidity. A surface without convexness can be directly coated in layers. Each layer at the start is the base layer and grows uniformly in thickness. Issues with convexed areas is removing the air, getting the film in the tighter space uniformly and building the layer in the space to the surface to allow for a uniform outer layer coating thickness. Extra time is spent, smaller droplets sizes of coating spray may be required, more plasticizer needed to allow the film to bridge without cracking if the crevice isn't filled and extra coating material is used.

In three dimensions it is also related to the extra volume associated with this convexed space. Which either coating fills or bridges over creating coating stress, imperfections and variation in coating amount needed to obtain a functional coating. Table 9 shows the solidity of the microspheres tested and FIG. 19 is a graph of the solidity of the various microspheres tested. The graph demonstrates the lack of solidity of the mannitol microspheres of the present invention (Mannosphere) and the narrow range of solidity in mannitol microsphere samples. A narrow range of solidity for the mannitol microspheres also aides in coating thickness consistency and direct coating layering. Maintaining the film surface contour. It is apparent in the SEMs the crevices in the MCell 400 beads as well as the separation in the Freund beads made by a similar granulation route would require additional coating material to fill these spaces. The SURESPHERES® and the PHARM-A-SPHERE™ beads would lose coating material into the contour of the risers.

TABLE 9

Solidity ratio of the microspheres tested

| Material | Maker | Lot | Solidity % > 0.99 |
|---|---|---|---|
| Mannospheres | SPI Pharma | 10/7/11-4 | 96.7% |
| SURESPHERES ® 20/25 | Colorcon | ST502051 | 14.0% |
| MCell 400 T | Pharmatrans Sanaq AG | 5100824001 | 2.5% |
| PHARM-A-SPHERE ™ | Werner | 08010002 | 0.02% |

Convexity

The microspheres of the present invention and current commercial microspheres/beads were also examined for convexity. Convexity is similar to solidity but focuses more on surface smoothness. Here the most accurate measurement is the periphery of the particle. What the approximation is in this index is the cord length that is drawn surrounding the particle which is the same cord length as in the solidity measurement. If the surface is perfectly smooth and without crevices or risers the convexity will be equal to one. Convexity is calculated in accordance with International Organization for Standardization (ISO) 9276-6 (2008). See, e.g., FIG. 23. Table 10 shows the convexity ratio of the microspheres tested and FIG. 20 is a graph of the convexity ratio of the various microspheres tested. Note the forecasted surface to be coated is consistent with a smoothed surface without risers or crevices for 96% of the particles at a convexity factor of 0.99. It is apparent in the table that the effective surface area for coating is lost in area difference between the area of a perfectly spherical shape and into either crevice or riser imperfections. The difference at a scale of comparison at 0.99 is substantial.

TABLE 10

Convexity ratio of the microspheres tested

| Material | Maker | Lot | Convexity % > 0.99 |
|---|---|---|---|
| Mannospheres | SPI Pharma | 10/7/11-4 | 81.2% |
| SURESPHERES ® 20/25 | Colorcon | ST502051 | 9.0% |
| MCell 400 T | Pharmatrans Sanaq AG | 5100824001 | 12.6% |
| PHARM-A-SPHERE ™ | Werner | 08010002 | 0.02% |

Risers cause coating thickness variation by generating local spots of thin coating or pin holes. If a functional coat must be 10 μm thick and pin holes need to be avoided then the coating over the riser needs to be 10 μm thick. Making the coating in other regions required to be thicker. Mannospheres surface has uniform risers which coating materials can grip to hold onto. These risers have a <2 μm depth and thus contribute little to coating thickness variability. See, e.g., FIGS. 24 and 25.

Example 3

Erythritol EP (Baolingbao Biology Co., LTD., China) was added to a Tornado Spin Disc (Gold Metal Cincinnati Ohio). The units spin head was heated to ~160° C. while spinning at 3400 RPM and made microspheres with a PSD of d(0.1)=131 μm, a d(0.5)=262 μm and a d(0.9)=371 μm. The size distribution ratio is 2.8 to 1 for this run. The DSC of these beads shows a single and sharp melt peak at 121.6° C. with a heat of fusion of 273.1 J/g. A pure crystalline erythritol melt range of 199° C. to 121° C. is expected and thus crystal structure of formed microsphere is a standard and highest energy erythritol polymorph.

We claim:

1. A microsphere comprising a core material that is crystalline, wherein the microsphere has a circularity greater than 0.98 and an aspect ratio greater than 0.98, wherein the microsphere has a surface with ridges of 10 um or less, and wherein the microsphere has a moisture gain of less than 0.5% at 90% relative humidity.

2. The microsphere of claim 1, wherein the microsphere has a mean particle size from about 10 um to about 500 um.

3. The microsphere of claim 2, wherein the microsphere has a mean particle size from about 10 um to about 20 um.

4. The microsphere of claim 1, wherein the microsphere has a particle size distribution of 2.8 or less.

5. The microsphere of claim 4, wherein the microsphere has a particle size distribution of 2.0 or less.

6. The microsphere of claim 4, wherein the microsphere has a particle size distribution of 1.5 or less.

7. The microsphere of claim 4, wherein the microsphere has a particle size distribution of 1.0.

8. The microsphere of claim 1, wherein the microsphere has a skeletal density from about 1.4595 g/cc to about 1.4651 g/cc.

9. The microsphere of claim 1, wherein the microsphere has a moisture content of 0.5% or less.

10. The microsphere of claim 1, wherein the microsphere is water soluble.

11. The microsphere of claim 1, wherein the microsphere comprises a single core material.

12. The microsphere of claim 11, wherein the single core material is mannitol.

13. The microsphere of claim 1, wherein the microsphere comprises a 100% crystalline core.

14. The microsphere of claim 1, wherein the microsphere further comprises an active pharmaceutical ingredient.

15. The microsphere of claim 1, wherein the core material is a polyol.

16. The microsphere of claim 15, wherein the polyol is mannitol.

17. The microsphere of claim 1, wherein the microsphere lacks internal voids.

18. The microsphere of claim 1, wherein the microsphere has a moisture gain of less than 0.2% at 90% relative humidity.

19. A composition comprising the microsphere of claim 1.

20. The composition of claim 19, further comprising an active pharmaceutical ingredient.

* * * * *